United States Patent
Swift et al.

(10) Patent No.: US 7,947,765 B2
(45) Date of Patent: May 24, 2011

(54) BINDER AND WOOD BOARD PRODUCT FROM MAILLARD REACTANTS

(75) Inventors: Brian Lee Swift, Morristown, IN (US); Ruijian Xu, Indianapolis, IN (US); Ronald E. Kissell, Shelbyville, IN (US)

(73) Assignee: Knauf Insulation GmbH, Shelbyville, IN (US)

( * ) Notice: Subject to any disclaimer, the term of this patent is extended or adjusted under 35 U.S.C. 154(b) by 0 days.

(21) Appl. No.: 12/697,573

(22) Filed: Feb. 1, 2010

(65) Prior Publication Data
US 2010/0130649 A1 May 27, 2010

Related U.S. Application Data

(63) Continuation of application No. 11/657,963, filed on Jan. 25, 2007, now Pat. No. 7,655,711, which is a continuation of application No. 11/493,080, filed on Jul. 26, 2006.

(60) Provisional application No. 60/702,456, filed on Jul. 26, 2005, provisional application No. 60/743,071, filed on Dec. 22, 2005.

(51) Int. Cl.
*C08L 97/02* (2006.01)
*C08F 251/00* (2006.01)
(52) U.S. Cl. .......................................... 524/14; 527/312
(58) Field of Classification Search ................ 524/14; 527/312
See application file for complete search history.

(56) References Cited

U.S. PATENT DOCUMENTS

| | | | | |
|---|---|---|---|---|
| 1,801,052 A | * | 4/1931 | Meigs | 536/43 |
| 1,801,053 A | * | 4/1931 | Meigs | 524/734 |
| 1,886,353 A | * | 11/1932 | Novotny et al. | 527/303 |
| 2,392,105 A | * | 1/1946 | Sussman | 521/30 |
| 3,232,821 A | * | 2/1966 | Moore et al. | 442/326 |
| 3,802,897 A | * | 4/1974 | Voigt et al. | 106/209.1 |
| 3,809,664 A | * | 5/1974 | Fanta et al. | 527/312 |
| 3,826,767 A | * | 7/1974 | Hoover et al. | 527/312 |
| 3,856,606 A | * | 12/1974 | Fan et al. | 156/329 |
| 3,911,048 A | * | 10/1975 | Vargiu et al. | 525/40 |
| 4,028,290 A | * | 6/1977 | Reid | 524/768 |
| 4,048,127 A | * | 9/1977 | Gibbons et al. | 527/303 |
| 4,054,713 A | * | 10/1977 | Sakaguchi et al. | 442/327 |
| 4,097,427 A | * | 6/1978 | Aitken et al. | 527/312 |
| 4,107,379 A | * | 8/1978 | Stofko | 428/326 |
| 4,148,765 A | * | 4/1979 | Nelson | 525/7 |
| 4,183,997 A | * | 1/1980 | Stofko | 428/326 |
| 4,233,432 A | * | 11/1980 | Curtis, Jr. | 528/298 |
| 4,246,367 A | * | 1/1981 | Curtis, Jr. | 525/49 |
| 4,278,573 A | * | 7/1981 | Tessler | 527/312 |

(Continued)

FOREIGN PATENT DOCUMENTS

EP 0044614 1/1982

(Continued)

OTHER PUBLICATIONS

Ames, J. M., "The Maillard Browning Reaction—an Update", Chemistry & Industry, No. 17, 1988, 4 pages.

(Continued)

*Primary Examiner* — Mark Eashoo
*Assistant Examiner* — Liam J Heincer
(74) *Attorney, Agent, or Firm* — Barnes & Thornburg, LLP

(57) ABSTRACT

Binders to produce or promote cohesion in non or loosely assembled matter.

9 Claims, 6 Drawing Sheets

U.S. PATENT DOCUMENTS

| | | | |
|---|---|---|---|
| 4,296,173 A * | 10/1981 | Fahey | 428/378 |
| 4,301,310 A * | 11/1981 | Wagner | 568/863 |
| 4,322,523 A | 3/1982 | Wagner | |
| 4,330,443 A * | 5/1982 | Rankin | 527/312 |
| 4,357,194 A * | 11/1982 | Stofko | 156/308.6 |
| 4,400,496 A * | 8/1983 | Butler et al. | 527/312 |
| 4,464,523 A * | 8/1984 | Neigel et al. | 527/300 |
| 4,524,164 A * | 6/1985 | Viswanathan et al. | 524/14 |
| 4,668,716 A * | 5/1987 | Pepe et al. | 523/213 |
| 4,692,478 A * | 9/1987 | Viswanathan et al. | 527/300 |
| 4,754,056 A * | 6/1988 | Ansel et al. | 560/171 |
| 4,845,162 A * | 7/1989 | Schmitt et al. | 525/423 |
| 4,906,237 A * | 3/1990 | Johansson et al. | 604/265 |
| 4,912,147 A * | 3/1990 | Pfoehler et al. | 524/460 |
| 4,923,980 A * | 5/1990 | Blomberg | 536/55.2 |
| 5,037,930 A * | 8/1991 | Shih | 527/301 |
| 5,041,595 A * | 8/1991 | Yang et al. | 556/479 |
| 5,095,054 A * | 3/1992 | Lay et al. | 524/47 |
| 5,106,615 A * | 4/1992 | Dikstein | 424/78.04 |
| 5,114,004 A * | 5/1992 | Isono et al. | 206/222 |
| 5,124,369 A * | 6/1992 | Vandichel et al. | 521/155 |
| 5,151,465 A * | 9/1992 | Le-Khac | 524/544 |
| 5,308,896 A * | 5/1994 | Hansen et al. | 524/13 |
| 5,318,990 A * | 6/1994 | Strauss | 524/549 |
| 5,336,753 A * | 8/1994 | Jung et al. | 528/335 |
| 5,336,755 A * | 8/1994 | Pape | 528/486 |
| 5,340,868 A * | 8/1994 | Strauss et al. | 524/461 |
| 5,371,194 A | 12/1994 | Ferretti | |
| 5,387,665 A * | 2/1995 | Misawa et al. | 528/81 |
| 5,393,849 A * | 2/1995 | Srinivasan et al. | 525/425 |
| 5,434,233 A * | 7/1995 | Kiely et al. | 527/310 |
| 5,480,973 A * | 1/1996 | Goodlad et al. | 530/386 |
| 5,498,662 A * | 3/1996 | Tanaka et al. | 525/54.2 |
| 5,536,766 A * | 7/1996 | Seyffer et al. | 524/100 |
| 5,547,541 A * | 8/1996 | Hansen et al. | 162/12 |
| 5,571,618 A * | 11/1996 | Hansen et al. | 428/359 |
| 5,578,678 A * | 11/1996 | Hartmann et al. | 525/54.3 |
| 5,582,682 A * | 12/1996 | Ferretti | 162/10 |
| 5,583,193 A * | 12/1996 | Aravindakshan et al. | 527/300 |
| 5,609,727 A * | 3/1997 | Hansen et al. | 162/164.1 |
| 5,614,570 A * | 3/1997 | Hansen et al. | 524/13 |
| 5,620,940 A * | 4/1997 | Birbara et al. | 502/402 |
| 5,621,026 A * | 4/1997 | Tanaka et al. | 524/52 |
| 5,633,298 A * | 5/1997 | Arfaei et al. | 524/5 |
| 5,643,978 A * | 7/1997 | Darwin et al. | 524/5 |
| 5,645,756 A * | 7/1997 | Dubin et al. | 252/181 |
| 5,661,213 A * | 8/1997 | Arkens et al. | 524/555 |
| 5,691,060 A * | 11/1997 | Levy | 428/402.21 |
| 5,693,411 A * | 12/1997 | Hansen et al. | 442/417 |
| 5,756,580 A * | 5/1998 | Natori et al. | 525/100 |
| 5,807,364 A | 9/1998 | Hansen | |
| 5,855,987 A * | 1/1999 | Margel et al. | 428/195.1 |
| 5,885,337 A * | 3/1999 | Nohr et al. | 106/31.27 |
| 5,895,804 A * | 4/1999 | Lee et al. | 525/54.3 |
| 5,919,831 A * | 7/1999 | Philipp | 521/31 |
| 5,925,722 A * | 7/1999 | Exner et al. | 527/300 |
| 5,929,184 A * | 7/1999 | Holmes-Farley et al. | 526/290 |
| 5,932,344 A * | 8/1999 | Ikemoto et al. | 428/343 |
| 5,932,665 A * | 8/1999 | DePorter et al. | 525/381 |
| 5,932,689 A * | 8/1999 | Arkens et al. | 528/335 |
| 5,942,123 A * | 8/1999 | McArdle | 210/674 |
| 5,977,224 A * | 11/1999 | Cheung et al. | 524/249 |
| 5,977,232 A * | 11/1999 | Arkens et al. | 524/404 |
| 5,981,719 A * | 11/1999 | Woiszwillo et al. | 530/410 |
| 5,983,586 A * | 11/1999 | Berdan et al. | 52/407.3 |
| 5,990,216 A * | 11/1999 | Cai et al. | 524/423 |
| 6,072,086 A * | 6/2000 | James et al. | 568/449 |
| 6,077,883 A * | 6/2000 | Taylor et al. | 523/217 |
| 6,090,925 A * | 7/2000 | Woiszwillo et al. | 530/410 |
| 6,114,033 A * | 9/2000 | Ikemoto et al. | 428/343 |
| 6,114,464 A * | 9/2000 | Reck et al. | 525/329.5 |
| 6,136,916 A * | 10/2000 | Arkens et al. | 524/556 |
| 6,171,654 B1 * | 1/2001 | Salsman et al. | 427/389.8 |
| 6,210,472 B1 * | 4/2001 | Kwan et al. | 106/31.14 |
| 6,221,973 B1 * | 4/2001 | Arkens et al. | 525/327.7 |
| 6,310,227 B1 * | 10/2001 | Sarama et al. | 554/191 |
| 6,313,102 B1 * | 11/2001 | Colaco et al. | 514/53 |
| 6,319,683 B1 * | 11/2001 | James et al. | 435/40.5 |
| 6,331,350 B1 * | 12/2001 | Taylor et al. | 428/221 |
| 6,379,739 B1 * | 4/2002 | Formanek et al. | 426/650 |
| 6,395,856 B1 * | 5/2002 | Petty et al. | 528/24 |
| 6,440,204 B1 * | 8/2002 | Rogols et al. | 106/134.1 |
| 6,468,442 B2 * | 10/2002 | Bytnar | 252/70 |
| 6,468,730 B2 * | 10/2002 | Fujiwara et al. | 430/619 |
| 6,482,875 B2 | 11/2002 | Lorenz et al. | |
| 6,495,656 B1 * | 12/2002 | Haile et al. | 528/272 |
| 6,525,009 B2 * | 2/2003 | Sachdev et al. | 510/175 |
| 6,613,378 B1 * | 9/2003 | Erhan et al. | 426/658 |
| 6,638,882 B1 | 10/2003 | Helbing et al. | |
| 6,638,884 B2 * | 10/2003 | Quick et al. | 442/417 |
| 6,753,361 B2 * | 6/2004 | Kroner et al. | 524/14 |
| 6,852,247 B2 * | 2/2005 | Bytnar | 252/70 |
| 6,858,074 B2 * | 2/2005 | Anderson et al. | 106/724 |
| 6,861,495 B2 * | 3/2005 | Barsotti et al. | 528/272 |
| 6,864,044 B2 * | 3/2005 | Ishikawa et al. | 430/331 |
| 6,955,844 B2 * | 10/2005 | Tagge et al. | 428/53 |
| 7,029,717 B1 * | 4/2006 | Ojima et al. | 426/548 |
| 7,067,579 B2 | 6/2006 | Taylor et al. | |
| 7,090,745 B2 * | 8/2006 | Beckman et al. | 162/164.1 |
| 7,141,626 B2 * | 11/2006 | Rodrigues et al. | 525/328.2 |
| 7,195,792 B2 * | 3/2007 | Boston et al. | 426/268 |
| 7,201,778 B2 * | 4/2007 | Smith et al. | 8/115.51 |
| 2002/0032253 A1 * | 3/2002 | Lorenz et al. | 524/11 |
| 2002/0091185 A1 * | 7/2002 | Taylor et al. | 524/249 |
| 2002/0161108 A1 * | 10/2002 | Schultz et al. | 524/815 |
| 2003/0005857 A1 * | 1/2003 | Minami et al. | 106/162.71 |
| 2004/0019168 A1 * | 1/2004 | Soerens et al. | 526/271 |
| 2004/0033747 A1 * | 2/2004 | Miller et al. | 442/180 |
| 2004/0038017 A1 * | 2/2004 | Tutin et al. | 428/297.4 |
| 2004/0077055 A1 * | 4/2004 | Fosdick et al. | 435/85 |
| 2004/0122166 A1 * | 6/2004 | O'Brien-Bernini et al. | 525/54.31 |
| 2004/0152824 A1 * | 8/2004 | Dobrowolski | 524/494 |
| 2004/0249066 A1 * | 12/2004 | Heinzman et al. | 525/54.3 |
| 2004/0254285 A1 * | 12/2004 | Rodrigues et al. | 524/494 |
| 2005/0059770 A1 * | 3/2005 | Srinivasan et al. | 524/494 |
| 2005/0171085 A1 * | 8/2005 | Pinto et al. | 514/210.21 |
| 2005/0196421 A1 * | 9/2005 | Hunter et al. | 424/423 |
| 2005/0202224 A1 | 9/2005 | Helbing et al. | |
| 2005/0215153 A1 * | 9/2005 | Cossement et al. | 442/180 |
| 2005/0275133 A1 * | 12/2005 | Cabell et al. | 264/210.8 |
| 2006/0099870 A1 * | 5/2006 | Garcia et al. | 442/374 |
| 2006/0111480 A1 * | 5/2006 | Hansen et al. | 524/27 |
| 2006/0135433 A1 * | 6/2006 | Murray et al. | 514/15 |
| 2006/0252855 A1 * | 11/2006 | Pisanova et al. | 524/47 |
| 2007/0006390 A1 * | 1/2007 | Clamen et al. | 8/115.51 |
| 2007/0009582 A1 * | 1/2007 | Madsen et al. | 424/445 |
| 2007/0027283 A1 | 2/2007 | Swift et al. | |
| 2007/0123679 A1 | 5/2007 | Swift et al. | |
| 2008/0108741 A1 | 5/2008 | Van Herwijnen et al. | |

FOREIGN PATENT DOCUMENTS

| | | |
|---|---|---|
| EP | 0 524 518 | 7/1992 |
| EP | 0 547 819 | 12/1992 |
| EP | 0 583 086 | 7/1993 |
| EP | 0 672 720 | 3/1995 |
| EP | 0 714 754 | 6/1996 |
| EP | 0 826 710 | 8/1997 |
| EP | 0 873 976 | 4/1998 |
| EP | 0 882 756 | 12/1998 |
| EP | 0 911 361 | 4/1999 |
| EP | 0 990 729 | 4/2000 |
| EP | 1 038 433 | 9/2000 |
| EP | 1 193 288 | 9/2001 |
| EP | 1 225 193 | 7/2002 |
| EP | 1 486 547 | 6/2004 |
| EP | 1698598 | 9/2006 |
| FR | 2 614 388 | 10/1988 |
| GB | 2 078 805 | 1/1982 |
| JP | 57-101100 | 6/1982 |
| JP | 58-11193 | 1/1983 |
| JP | 3-173680 | 7/1991 |
| JP | 7-34023 | 2/1995 |
| JP | 2002-293576 | 9/2002 |
| JP | 2004-60058 | 2/2004 |
| SU | 374400 | 3/1973 |
| WO | 99/47765 | 9/1999 |

| WO | 00/62628 | 10/2000 |
| WO | 03/071879 | 9/2003 |
| WO | 2004/076734 | 9/2004 |
| WO | 2006/044302 | 4/2006 |
| WO | 2006/136614 | 12/2006 |
| WO | 2007/014236 | 2/2007 |
| WO | 2007/024020 | 3/2007 |

OTHER PUBLICATIONS

"Gamma-aminopropyltrimethoxysilane", Hawley's Condensed Chemical Dictionary, 14th Edition, John Wiley & Sons, Inc., 2002, 1 page.

English Translation of Japanese Abstract for 58011193, Jan. 21, 1983, 1 page.

English Translation of Japanese Abstract for 03173680, Jul. 26, 1991, 1 page.

English Translation of Japanese Abstract for 07034023, Feb. 3, 1995, 1 page.

English Translation of Russian Abstract for 374400, Mar. 20, 1973, 1 page.

English Translation of Japanese Abstract for 2004-60058, Feb. 26, 2004, 1 page.

English Translation of French Abstract for 2614388, Oct. 28, 1988, 1 page.

English Translation of Japanese Abstract for 2002-293576, Oct. 9, 2002, 2 page.

English Translation of Japanese Abstract for 57-101100, Jun. 23, 1982, 1 page.

English Translation of European Abstract for 1038433, Sep. 27, 2000, 1 page.

International Search Report and Written Opinion for PCT/EP2008/060178, Completed Oct. 14, 2008.

International Search Report and Written Opinion for PCT/US2008/059730, completed Sep. 16, 2008.

Hodge, J.E., Chemistry of Browning Reactions in Model Systems,: 1953, J. Argic. Food Chem., vol. 1, No. 15, pp. 928-943.

International Search Report and Written Opinion for PCT/US2008/069046, completed Sep. 22, 2008.

* cited by examiner

BINDER AND WOOD BOARD PRODUCT FROM MAILLARD REACTANTS

CROSS-REFERENCE TO RELATED APPLICATIONS

This application is a continuation of U.S. patent application Ser. No. 11/657,963, filed Jan. 25, 2007, which is a continuation of U.S. patent application Ser. No. 11/493,080, filed Jul. 26, 2006, which claims the benefit under 35 U.S.C. §119 (e) of U.S. provisional application Ser. No. 60/702,456, filed Jul. 26, 2005, and U.S. provisional application Ser. No. 60/743,071, filed Dec. 22, 2005, the disclosures of which are hereby incorporated herein by reference.

BACKGROUND

Binders are useful in fabricating materials from non or loosely assembled matter. For example, binders enable two or more surfaces to become united. Binders may be broadly classified into two main groups: organic and inorganic, with the organic materials being subdivided into those of animal, vegetable, and synthetic origin. Another way of classifying binders is based upon the chemical nature of these compounds: (1) protein or protein derivatives; (2) starch, cellulose, or gums and their derivatives; (3) thermoplastic synthetic resins; (4) thermosetting synthetic resins; (5) natural resins and bitumens; (6) natural and synthetic rubbers; and (7) inorganic binders. Binders also may be classified according to the purpose for which they are used: (1) bonding rigid surfaces, such as, rigid plastics, and metals; and (2) bonding flexible surfaces, such as, flexible plastics and thin metallic sheets, among others.

Thermoplastic binders comprise a variety of polymerized materials such as polyvinyl acetate, polyvinyl butyral, polyvinyl alcohol, and other polyvinyl resins; polystyrene resins; acrylic and methacrylic acid ester resins; cyanoacrylates; and various other synthetic resins such as polyisobutylene polyamides, courmarone-idene products, and silicones. Such thermoplastic binders may have permanent solubility and fusibility so that they creep under stress and soften when heated. They are used for the manufacturing various products, for example, tapes.

Thermosetting binders comprise a variety of phenol-aldehyde, urea-aldehyde, melamine-aldehyde, and other condensation-polymerization materials like the furane and polyurethane resins. Thermosetting binders may be characterized by being transformed into insoluble and infusible materials by means of either heat or catalytic action. Binder compositions containing phenol-, resorcinol-, urea-, melamine-formaldehyde, phenolfurfuraldehyde, and the like are used for the bonding of textiles, plastics, rubbers, and many other materials.

As indicated above, binders are useful in fabricating materials from non or loosely assembled matter. Accordingly, compositions capable of functioning as a binder are desirable.

SUMMARY

Cured or uncured binders in accordance with an illustrative embodiment of the present invention may comprise one or more of the following features or combinations thereof. In addition, materials in accordance with the present invention may comprise one or more of the following features or combinations thereof:

Initially it should be appreciated that the binders of the present invention may be utilized in a variety of fabrication applications to produce or promote cohesion in a collection of non or loosely assembled matter. A collection includes two or more components. The binders produce or promote cohesion in at least two of the components of the collection. For example, subject binders are capable of holding a collection of matter together such that the matter adheres in a manner to resist separation. The binders described herein can be utilized in the fabrication of any material.

One potential feature of the present binders is that they are formaldehyde free. Accordingly, the materials the binders are disposed upon may also be formaldehyde free, (e.g. fiberglass). In addition, the present binders may have a reduced trimethylamine content as compared to other known binders.

With respect to the present binder's chemical constituents, they may include ester and/or polyester compounds. The binders may include ester and/or polyester compounds in combination with a vegetable oil, such as soybean oil. Furthermore, the binders may include ester and/or polyester compounds in combination with sodium salts of organic acids. The binders may include sodium salts of inorganic acids. The binders may also include potassium salts of organic acids. Moreover, the binders may include potassium salts of inorganic acids. The described binders may include ester and/or polyester compounds in combination with a clay additive, such as montmorillonite.

Furthermore, the binders of the present invention may include a product of a Maillard reaction. For example, see FIG. 2. As shown in FIG. 2, Maillard reactions produce melanoidins, i.e., high molecular weight, furan ring and nitrogen-containing polymers that vary in structure depending on the reactants and conditions of their preparation. Melanoidins display a C:N ratio, degree of unsaturation, and chemical aromaticity that increase with temperature and time of heating. (See, Ames, J. M. in "The Maillard Browning Reaction—an update," Chemistry and Industry (Great Britain), 1988, 7, 558-561, the disclosure of which is hereby incorporated herein by reference). Accordingly, the subject binders may be made via a Maillard reaction and thus contain melanoidins. It should be appreciated that the subject binders may contain melanoidins, or other Maillard reaction products, which products are generated by a separate process and then simply added to the composition that makes up the binder. The melanoidins in the binder may be water-insoluble. Moreover, the binders may be thermoset binders.

The Maillard reactants to produce a melanoidin may include an amine reactant reacted with a reducing-sugar carbohydrate reactant. For example, an ammonium salt of a monomeric polycarboxylic acid may be reacted with (i) a monosaccharide in its aldose or ketose form or (ii) a polysaccharide or (iii) with combinations thereof. In another variation, an ammonium salt of a polymeric polycarboxylic acid may be contacted with (i) a monosaccharide in its aldose or ketose form or (ii) a polysaccharide, or (iii) with combinations thereof. In yet another variation, an amino acid may be contacted with (i) a monosaccharide in its aldose or ketose form, or (ii) with a polysaccharide or (iii) with combinations thereof. Furthermore, a peptide may be contacted with (i) a monosaccharide in its aldose or ketose form or (ii) with a polysaccharide or (iii) with combinations thereof. Moreover, a protein may be contacted with (i) a monosaccharide in its aldose or ketose form or (ii) with a polysaccharide or (iii) with combinations thereof.

It should also be appreciated that the binders of the present invention may include melanoidins produced in non-sugar variants of Maillard reactions. In these reactions an amine reactant is contacted with a non-carbohydrate carbonyl reactant. In one illustrative variation, an ammonium salt of a monomeric polycarboxylic acid is contacted with a non-carbohydrate carbonyl reactant such as, pyruvaldehyde, acetaldehyde, crotonaldehyde, 2-furaldehyde, quinone, ascorbic acid, or the like, or with combinations thereof. In another variation, an ammonium salt of a polymeric polycarboxylic acid may be contacted with a non-carbohydrate carbonyl reactant such as, pyruvaldehyde, acetaldehyde, crotonaldehyde, 2-furaldehyde, quinone, ascorbic acid, or the like, or with combinations thereof. In yet another illustrative variation, an amino acid may be contacted with a non-carbohydrate carbonyl reactant such as, pyruvaldehyde, acetaldehyde, crotonaldehyde, 2-furaldehyde, quinone, ascorbic acid, or the like, or with combinations thereof. In another illustrative variation, a peptide may be contacted with a non-carbohydrate carbonyl reactant such as, pyruvaldehyde, acetaldehyde, crotonaldehyde, 2-furaldehyde, quinone, ascorbic acid, or the like, or with combinations thereof. In still another illustrative variation, a protein may contacted with a non-carbohydrate carbonyl reactant such as, pyruvaldehyde, acetaldehyde, crotonaldehyde, 2-furaldehyde, quinone, ascorbic acid, and the like, or with combinations thereof.

The melanoidins discussed herein may be generated from melanoidin reactant compounds. These reactant compounds are disposed in an aqueous solution at an alkaline pH and therefore are not corrosive. That is, the alkaline solution prevents or inhibits the eating or wearing away of a substance, such as metal, caused by chemical decomposition brought about by, for example, an acid. The reactant compounds may include a reducing-sugar carbohydrate reactant and an amine reactant. In addition, the reactant compounds may include a non-carbohydrate carbonyl reactant and an amine reactant.

It should also be understood that the binders described herein may be made from melanoidin reactant compounds themselves. That is, once the Maillard reactants are mixed, this mixture can function as a binder of the present invention. These binders may be utilized to fabricate uncured, formaldehyde-free matter, such as fibrous materials.

In the alternative, a binder made from the reactants of a Maillard reaction may be cured. These binders may be used to fabricate cured formaldehyde-free matter, such as, fibrous compositions. These compositions are water-resistant and, as indicated above, include water-insoluble melanoidins.

It should be appreciated that the binders described herein may be used in manufacturing products from a collection of non or loosely assembled matter. For example, these binders may be employed to fabricate fiber products. These products may be made from woven or nonwoven fibers. The fibers can be heat-resistant or non heat-resistant fibers or combinations thereof. In one illustrative embodiment, the binders are used to bind glass fibers to make fiberglass. In another illustrative embodiment, the binders are used to make cellulosic compositions. With respect to cellulosic compositions, the binders may be used to bind cellulosic matter to fabricate, for example, wood fiber board which has desirable physical properties (e.g., mechanical strength).

One embodiment of the invention is directed to a method for manufacturing products from a collection of non-or loosely assembled matter. One example of using this method is in the fabrication of fiberglass. However, as indicated above this method can be utilized in the fabrication of any material, as long as the method produces or promotes cohesion when utilized. The method may include contacting the fibers with a thermally-curable, aqueous binder. The binder may include (i) an ammonium salt of a polycarboxylic acid reactant and (ii) a reducing-sugar carbohydrate reactant. These two reactants are melanoidin reactants (i.e. these reactants produce melanoidins when reacted under conditions to initiate a Maillard reaction.) The method can further include removing water from the binder in contact with the fibers (i.e., the binder is dehydrated). The method can also include curing the binder in contact with the glass fibers (e.g. thermally curing the binder).

Another example of utilizing this method is in the fabrication of cellulosic materials. The method may include contacting the cellulosic material (e.g., cellulose fibers) with a thermally-curable, aqueous binder. The binder may include (i) an ammonium salt of a polycarboxylic acid reactant and (ii) a reducing-sugar carbohydrate reactant. As indicated above, these two reactants are melanoidin reactant compounds. The method can also include removing water from the binder in contact with the cellulosic material. As before, the method can also include curing the binder (e.g. thermal curing).

One way of using the binders is to bind glass fibers together such that they become organized into a fiberglass mat. The mat of fiberglass may be processed to form one of several types of fiberglass materials, such as fiberglass insulation. In one example, the fiberglass material may have glass fibers present in the range from about 80% to about 99% by weight. The uncured binder may function to hold the glass fibers together. The cured binder may function to hold the glass fibers together.

In addition, a fibrous product is described that includes a binder in contact with cellulose fibers, such as those in a mat of wood shavings or sawdust. The mat may be processed to form one of several types of wood fiber board products. In one variation, the binder is uncured. In this variation, the uncured binder may function to hold the cellulosic fibers together. In the alternative, the cured binder may function to hold the cellulosic fibers together.

Additional features of the present invention will become apparent to those skilled in the art upon consideration of the following detailed description of illustrative embodiments exemplifying the best mode of carrying out the invention as presently perceived.

DETAILED DESCRIPTION

Figure 1:
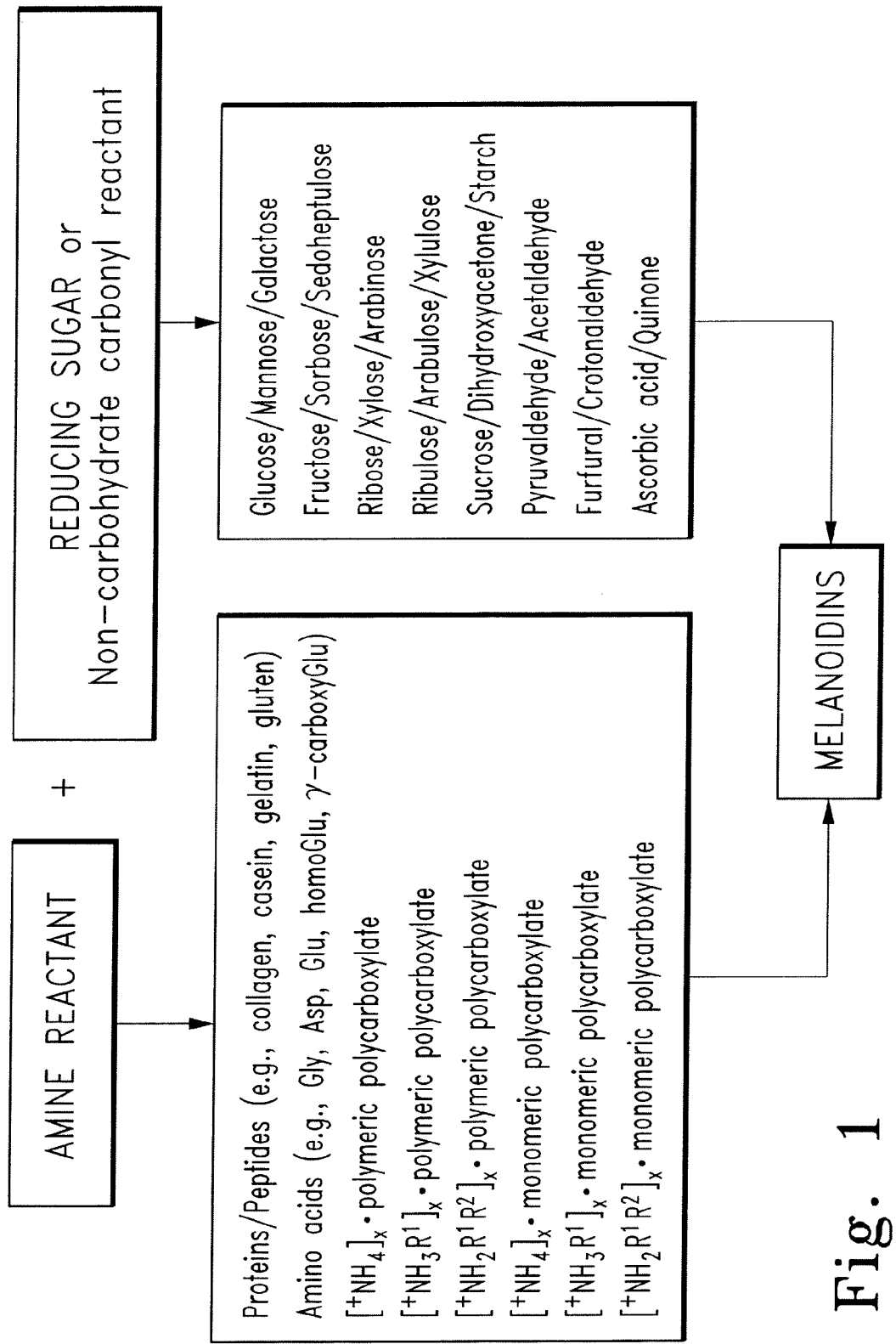
FIG. 1 shows a number of illustrative reactants for producing melanoidins.

While the invention is susceptible to various modifications and alternative forms, specific embodiments will herein be described in detail. It should be understood, however, that there is no intent to limit the invention to the particular forms described, but on the contrary, the intention is to cover all modifications, equivalents, and alternatives falling within the spirit and scope of the invention.

As used herein, the phrase "formaldehyde-free" means that a binder or a material that incorporates a binder liberates less than about 1 ppm formaldehyde as a result of drying and/or curing. The 1 ppm is based on the weight of sample being measured for formaldehyde release.

Cured indicates that the binder has been exposed to conditions to so as to initiate a chemical change. Examples of these chemical changes include, but are not limited to, (i) covalent bonding, (ii) hydrogen bonding of binder components, and chemically cross-linking the polymers and/or oligomers in the binder. These changes may increase the binder's durability and solvent resistance as compared to the uncured binder. Curing a binder may result in the formation of a thermoset material. Furthermore, curing may include the generation of melanoidins. These melanoidins may be generated from a Maillard reaction from melanoidin reactant compounds. In addition, a cured binder may result in an increase in adhesion between the matter in a collection as compared to an uncured binder. Curing can be initiated by, for example, heat, electromagnetic radiation or, electron beams.

In a situation where the chemical change in the binder results in the release of water, e.g. polymerization and cross-linking, a cure can be determined by the amount of water released above that would occur from drying alone. The techniques used to measure the amount of water released during drying as compared to when a binder is cured, are well known in the art.

In accordance with the above paragraph, an uncured binder is one that has not been cured.

As used herein, the term "alkaline" indicates a solution having a pH that is greater than or equal to about 7. For example, the pH of the solution can be less than or equal to about 10. In addition, the solution may have a pH from about 7 to about 10, or from about 8 to about 10, or from about 9 to about 10.

As used herein, the term "ammonium" includes, but is not limited to, $^+NH_4$, $^+NH_3R^1$, and $^+NH_2R^1R^2$, where $R^1$ and $R^2$ are each independently selected in $^+NH_2R^1R^2$, and where $R^1$ and $R^2$ are selected from alkyl, cycloalkyl, alkenyl, cycloalkenyl, heterocyclyl, aryl, and heteroaryl.

The term "alkyl" refers to a saturated monovalent chain of carbon atoms, which may be optionally branched; the term "cycloalkyl" refers to a monovalent chain of carbon atoms, a portion of which forms a ring; the term "alkenyl" refers to an unsaturated monovalent chain of carbon atoms including at least one double bond, which may be optionally branched; the term "cycloalkenyl" refers to an unsaturated monovalent chain of carbon atoms, a portion of which forms a ring; the term "heterocyclyl" refers to a monovalent chain of carbon and heteroatoms, wherein the heteroatoms are selected from nitrogen, oxygen, and sulfur, a portion of which, including at least one heteroatom, form a ring; the term "aryl" refers to an aromatic mono or polycyclic ring of carbon atoms, such as phenyl, naphthyl, and the like; and the term "heteroaryl" refers to an aromatic mono or polycyclic ring of carbon atoms and at least one heteroatom selected from nitrogen, oxygen, and sulfur, such as pyridinyl, pyrimidinyl, indolyl, benzoxazolyl, and the like. It is to be understood that each of alkyl, cycloalkyl, alkenyl, cycloalkenyl, and heterocyclyl may be optionally substituted with independently selected groups such as alkyl, haloalkyl, hydroxyalkyl, aminoalkyl, carboxylic acid and derivatives thereof, including esters, amides, and nitriles, hydroxy, alkoxy, acyloxy, amino, alkyl and dialkylamino, acylamino, thio, and the like, and combinations thereof. It is further to be understood that each of aryl and heteroaryl may be optionally substituted with one or more independently selected substituents, such as halo, hydroxy, amino, alkyl or dialkylamino, alkoxy, alkylsulfonyl, cyano, nitro, and the like.

As used herein, the term "polycarboxylic acid" indicates a dicarboxylic, tricarboxylic, tetracarboxylic, pentacarboxylic, and like monomeric polycarboxylic acids, and anhydrides, and combinations thereof, as well as polymeric polycarboxylic acids, anhydrides, copolymers, and combinations thereof. In one aspect, the polycarboxylic acid ammonium salt reactant is sufficiently non-volatile to maximize its ability to remain available for reaction with the carbohydrate reactant of a Maillard reaction (discussed below). In another aspect, the polycarboxylic acid ammonium salt reactant may be substituted with other chemical functional groups.

Illustratively, a monomeric polycarboxylic acid may be a dicarboxylic acid, including, but not limited to, unsaturated aliphatic dicarboxylic acids, saturated aliphatic dicarboxylic acids, aromatic dicarboxylic acids, unsaturated cyclic dicarboxylic acids, saturated cyclic dicarboxylic acids, hydroxy-substituted derivatives thereof, and the like. Or, illustratively, the polycarboxylic acid(s) itself may be a tricarboxylic acid, including, but not limited to, unsaturated aliphatic tricarboxylic acids, saturated aliphatic tricarboxylic acids, aromatic tricarboxylic acids, unsaturated cyclic tricarboxylic acids, saturated cyclic tricarboxylic acids, hydroxy-substituted derivatives thereof, and the like. It is appreciated that any such polycarboxylic acids may be optionally substituted, such as with hydroxy, halo, alkyl, alkoxy, and the like. In one variation, the polycarboxylic acid is the saturated aliphatic tricarboxylic acid, citric acid. Other suitable polycarboxylic acids are contemplated to include, but are not limited to, aconitic acid, adipic acid, azelaic acid, butane tetracarboxylic acid dihydride, butane tricarboxylic acid, chlorendic acid, citraconic acid, dicyclopentadiene-maleic acid adducts, diethylenetriamine pentaacetic acid, adducts of dipentene and maleic acid, ethylenediamine tetraacetic acid (EDTA), fully maleated rosin, maleated tall-oil fatty acids, fumaric acid, glutaric acid, isophthalic acid, itaconic acid, maleated rosin oxidized with potassium peroxide to alcohol then carboxylic acid, maleic acid, malic acid, mesaconic acid, biphenol A or bisphenol F reacted via the KOLBE-Schmidt reaction with carbon dioxide to introduce 3-4 carboxyl groups, oxalic acid, phthalic acid, sebacic acid, succinic acid, tartaric acid, terephthalic acid, tetrabromophthalic acid, tetrachlorophthalic acid, tetrahydrophthalic acid, trimellitic acid, trimesic acid, and the like, and anhydrides, and combinations thereof.

Illustratively, a polymeric polycarboxylic acid may be an acid, for example, polyacrylic acid, polymethacrylic acid, polymaleic acid, and like polymeric polycarboxylic acids, copolymers thereof, anhydrides thereof, and mixtures thereof. Examples of commercially available polyacrylic acids include AQUASET-529 (Rohm & Haas, Philadelphia, Pa., USA), CRITERION 2000 (Kemira, Helsinki, Finland, Europe), NF1 (H. B. Fuller, St. Paul, Minn., USA), and SOKALAN (BASF, Ludwigshafen, Germany, Europe). With respect to SOKALAN, this is a water-soluble polyacrylic copolymer of acrylic acid and maleic acid, having a molecular weight of approximately 4000. AQUASET-529 is a composition containing polyacrylic acid cross-linked with glycerol, also containing sodium hypophosphite as a catalyst. CRITERION 2000 is an acidic solution of a partial salt of polyacrylic acid, having a molecular weight of approximately 2000. With respect to NF1, this is a copolymer containing carboxylic acid functionality and hydroxy functionality, as well as units with neither functionality; NF1 also contains chain transfer agents, such as sodium hypophosphite or organophosphate catalysts.

Further, compositions including polymeric polycarboxylic acids are also contemplated to be useful in preparing the binders described herein, such as those compositions described in U.S. Pat. Nos. 5,318,990, 5,661,213, 6,136,916, and 6,331,350, the disclosures of which are hereby incorporated herein by reference. In particular, in U.S. Pat. Nos. 5,318,990 and 6,331,350 an aqueous solution of a polymeric polycarboxylic acid, a polyol, and a catalyst is described.

As described in U.S. Pat. Nos. 5,318,990 and 6,331,350, the polymeric polycarboxylic acid comprises an organic polymer or oligomer containing more than one pendant carboxy group. The polymeric polycarboxylic acid may be a homopolymer or copolymer prepared from unsaturated carboxylic acids including, but not necessarily limited to, acrylic acid, methacrylic acid, crotonic acid, isocrotonic acid, maleic acid, cinnamic acid, 2-methylmaleic acid, itaconic acid, 2-methylitaconic acid, $\alpha,\beta$-methyleneglutaric acid, and the like. Alternatively, the polymeric polycarboxylic acid may be prepared from unsaturated anhydrides including, but not necessarily limited to, maleic anhydride, itaconic anhydride, acrylic anhydride, methacrylic anhydride, and the like, as well as mixtures thereof. Methods for polymerizing these acids and anhydrides are well-known in the chemical art. The polymeric polycarboxylic acid may additionally comprise a copolymer of one or more of the aforementioned unsaturated carboxylic acids or anhydrides and one or more vinyl compounds including, but not necessarily limited to, styrene, $\alpha$-methylstyrene, acrylonitrile, methacrylonitrile, methyl acrylate, ethyl acrylate, n-butyl acrylate, isobutyl acrylate, methyl methacrylate, n-butyl methacrylate, isobutyl methacrylate, glycidyl methacrylate, vinyl methyl ether, vinyl acetate, and the like. Methods for preparing these copolymers are well-known in the art. The polymeric polycarboxylic acids may comprise homopolymers and copolymers of polyacrylic acid. The molecular weight of the polymeric polycarboxylic acid, and in particular polyacrylic acid polymer, may be is less than 10000, less than 5000, or about 3000 or less. For example, the molecular weight may be 2000.

As described in U.S. Pat. Nos. 5,318,990 and 6,331,350, the polyol (in a composition including a polymeric polycarboxylic acid) contains at least two hydroxyl groups. The polyol should be sufficiently nonvolatile such that it will substantially remain available for reaction with the polymeric polycarboxylic acid in the composition during heating and curing operations. The polyol may be a compound with a molecular weight less than about 1000 bearing at least two hydroxyl groups such as, ethylene glycol, glycerol, pentaerythritol, trimethylol propane, sorbitol, sucrose, glucose, resorcinol, catechol, pyrogallol, glycollated ureas, 1,4-cyclohexane diol, diethanolamine, triethanolamine, and certain reactive polyols, for example, $\beta$-hydroxyalkylamides such as, for example, bis[N,N-di ($\beta$-hydroxyethyl)]adipamide, or it may be an addition polymer containing at least two hydroxyl groups such as, polyvinyl alcohol, partially hydrolyzed polyvinyl acetate, and homopolymers or copolymers of hydroxyethyl(meth)acrylate, hydroxypropyl(meth)acrylate, and the like.

As described in U.S. Pat. Nos. 5,318,990 and 6,331,350, the catalyst (in a composition including a polymeric polycarboxylic acid) is a phosphorous-containing accelerator which may be a compound with a molecular weight less than about 1000 such as, an alkali metal polyphosphate, an alkali metal dihydrogen phosphate, a polyphosphoric acid, and an alkyl phosphinic acid or it may be an oligomer or polymer bearing phosphorous-containing groups, for example, addition polymers of acrylic and/or maleic acids formed in the presence of sodium hypophosphite, addition polymers prepared from ethylenically unsaturated monomers in the presence of phosphorous salt chain transfer agents or terminators, and addition polymers containing acid-functional monomer residues, for example, copolymerized phosphoethyl methacrylate, and like phosphonic acid esters, and copolymerized vinyl sulfonic acid monomers, and their salts. The phosphorous-containing accelerator may be used at a level of from about 1% to about 40%, by weight based on the combined weight of the polymeric polycarboxylic acid and the polyol. A level of phosphorous-containing accelerator of from about 2.5% to about 10%, by weight based on the combined weight of the polymeric polycarboxylic acid and the polyol may be used. Examples of such catalysts include, but are not limited to, sodium hypophosphite, sodium phosphite, potassium phosphite, disodium pyrophosphate, tetrasodium pyrophosphate, sodium tripolyphosphate, sodium hexametaphosphate, potassium phosphate, potassium polymetaphosphate, potassium polyphosphate, potassium tripolyphosphate, sodium trimetaphosphate, and sodium tetrametaphosphate, as well as mixtures thereof.

Compositions including polymeric polycarboxylic acids described in U.S. Pat. Nos. 5,661,213 and 6,136,916 that are contemplated to be useful in preparing the binders described herein comprise an aqueous solution of a polymeric polycarboxylic acid, a polyol containing at least two hydroxyl groups, and a phosphorous-containing accelerator, wherein the ratio of the number of equivalents of carboxylic acid groups, to the number of equivalents of hydroxyl groups is from about 1:0.01 to about 1:3

As disclosed in U.S. Pat. Nos. 5,661,213 and 6,136,916, the polymeric polycarboxylic acid may be, a polyester containing at least two carboxylic acid groups or an addition polymer or oligomer containing at least two copolymerized carboxylic acid-functional monomers. The polymeric polycarboxylic acid is preferably an addition polymer formed from at least one ethylenically unsaturated monomer. The addition polymer may be in the form of a solution of the addition polymer in an aqueous medium such as, an alkali-soluble resin which has been solubilized in a basic medium; in the form of an aqueous dispersion, for example, an emulsion-polymerized dispersion; or in the form of an aqueous suspension. The addition polymer must contain at least two carboxylic acid groups, anhydride groups, or salts thereof. Ethylenically unsaturated carboxylic acids such as, methacrylic acid, acrylic acid, crotonic acid, fumaric acid, maleic acid, 2-methyl maleic acid, itaconic acid, 2-methyl itaconic acid, $\alpha,\beta$-methylene glutaric acid, monoalkyl maleates, and monoalkyl fumarates; ethylenically unsaturated anhydrides, for example, maleic anhydride, itaconic anhydride, acrylic anhydride, and methacrylic anhydride; and salts thereof, at a level of from about 1% to 100%, by weight, based on the weight of the addition polymer, may be used. Additional ethylenically unsaturated monomer may include acrylic ester monomers including methyl acrylate, ethyl acrylate, butyl acrylate, 2-ethylhexyl acrylate, decyl acrylate, methyl methacrylate, butyl methacrylate, isodecyl methacrylate, hydroxyethyl acrylate, hydroxyethyl methacrylate, and hydroxypropyl methacrylate; acrylamide or substituted acrylamides; styrene or substituted styrenes; butadiene; vinyl acetate or other vinyl esters; acrylonitrile or methacrylonitrile; and the like. The addition polymer containing at least two carboxylic acid groups, anhydride groups, or salts thereof may have a molecular weight from about 300 to about 10,000,000. A molecular weight from about 1000 to about 250,000 may be used. When the addition polymer is an alkali-soluble resin having a carboxylic acid, anhydride, or salt thereof, content of from about 5% to about 30%, by weight based on the total weight of the addition polymer, a molecular weight from about 10,000 to about 100,000 may be utilized Methods for preparing these additional polymers are well-known in the art.

As described in U.S. Pat. Nos. 5,661,213 and 6,136,916, the polyol (in a composition including a polymeric polycarboxylic acid) contains at least two hydroxyl groups and should be sufficiently nonvolatile that it remains substantially available for reaction with the polymeric polycarboxylic acid in the composition during heating and curing operations. The polyol may be a compound with a molecular weight less than about 1000 bearing at least two hydroxyl groups, for example, ethylene glycol, glycerol, pentaerythritol, trimethylol propane, sorbitol, sucrose, glucose, resorcinol, catechol, pyrogallol, glycollated ureas, 1,4-cyclohexane diol, diethanolamine, triethanolamine, and certain reactive polyols, for example, β-hydroxyalkylamides, for example, bis-[N,N-di (β-hydroxyethyl)]adipamide, bis[N,N-di(β-hydroxypropyl)] azelamide, bis[N—N-di(β-hydroxypropyl)]adipamide, bis [N—N-di (β-hydroxypropyl)]glutaramide, bis[N—N-di(β-hydroxypropyl)]succinamide, and bis[N-methyl-N-(β-hydroxyethyl)]oxamide, or it may be an addition polymer containing at least two hydroxyl groups such as, polyvinyl alcohol, partially hydrolyzed polyvinyl acetate, and homopolymers or copolymers of hydroxyethyl (meth)acrylate, hydroxypropyl (meth)acrylate, and the like.

As described in U.S. Pat. Nos. 5,661,213 and 6,136,916, the phosphorous-containing accelerator (in a composition including a polymeric polycarboxylic acid) may be a compound with a molecular weight less than about 1000 such as, an alkali metal hypophosphite salt, an alkali metal phosphite, an alkali metal polyphosphate, an alkali metal dihydrogen phosphate, a polyphosphoric acid, and an alkyl phosphinic acid or it may be an oligomer or polymer bearing phosphorous-containing groups such as, addition polymers of acrylic and/or maleic acids formed in the presence of sodium hypophosphite, addition polymers prepared from ethylenically unsaturated monomers in the presence of phosphorous salt chain transfer agents or terminators, and addition polymers containing acid-functional monomer residues such as, copolymerized phosphoethyl methacrylate, and like phosphonic acid esters, and copolymerized vinyl sulfonic acid monomers, and their salts. The phosphorous-containing accelerator may be used at a level of from about 1% to about 40%, by weight based on the combined weight of the polyacid and the polyol. A level of phosphorous-containing accelerator of from about 2.5% to about 10%, by weight based on the combined weight of the polyacid and the polyol, may be utilized.

As used herein, the term "amine base" includes, but is not limited to, ammonia, a primary amine, i.e., $NH_2R^1$, and a secondary amine, i.e., $NHR^1R^2$, where $R^1$ and $R^2$ are each independently selected in $NHR^1R^2$, and where $R^1$ and $R^2$ are selected from alkyl, cycloalkyl, alkenyl, cycloalkenyl, heterocyclyl, aryl, and heteroaryl, as defined herein. Illustratively, the amine base may be substantially volatile or substantially non-volatile under conditions sufficient to promote formation of the thermoset binder during thermal curing. Illustratively, the amine base may be a substantially volatile base, such as, ammonia, ethylamine, diethylamine, dimethylamine, and ethylpropylamine. Alternatively, the amine base may be a substantially non-volatile base, for example, aniline, 1-naphthylamine, 2-naphthylamine, and para-aminophenol.

As used herein, "reducing sugar" indicates one or more sugars that contain aldehyde groups, or that can isomerize, i.e., tautomerize, to contain aldehyde groups, which groups are reactive with an amino group under Maillard reaction conditions and which groups may be oxidized with, for example, $Cu^{+2}$ to afford carboxylic acids. It is also appreciated that any such carbohydrate reactant may be optionally substituted, such as with hydroxy, halo, alkyl, alkoxy, and the like. It is further appreciated that in any such carbohydrate reactant, one or more chiral centers are present, and that both possible optical isomers at each chiral center are contemplated to be included in the invention described herein. Further, it is also to be understood that various mixtures, including racemic mixtures, or other diastereomeric mixtures of the various optical isomers of any such carbohydrate reactant, as well as various geometric isomers thereof, may be used in one or more embodiments described herein.

As used herein, the term "fiberglass," indicates heat-resistant fibers suitable for withstanding elevated temperatures. Examples of such fibers include, but are not limited to, mineral fibers, aramid fibers, ceramic fibers, metal fibers, carbon fibers, polyimide fibers, certain polyester fibers, rayon fibers, and glass fibers. Illustratively, such fibers are substantially unaffected by exposure to temperatures above about 120° C.

FIG. 1 shows examples of reactants for a Maillard reaction. Examples of amine reactants include proteins, peptides, amino acids, ammonium salts of polymeric polycarboxylic acids, and ammonium salts of monomeric polycarboxylic acids. As illustrated, "ammonium" can be $[^{30}NH_4]_x$, $[^+NH_3R^1]_x$, and $[^+NH_2R^1R^2]_x$, where x is at least about 1. With respect to $^+NH_2R^1R^2$, $R^1$ and $R^2$ are each independently selected. Moreover, $R^1$ and $R^2$ are selected from alkyl, cycloalkyl, alkenyl, cycloalkenyl, heterocyclyl, aryl, and heteroaryl, as described above. FIG. 1 also illustrates examples of reducing-sugar reactants for producing melanoidins, including monosaccharides, in their aldose or ketose form, polysaccharides, or combinations thereof. Illustrative non-carbohydrate carbonyl reactants for producing melanoidins are also shown in FIG. 1 and include various aldehydes, e.g., pyruvaldehyde and furfural, as well as compounds such as ascorbic acid and quinone.

Figure 2:
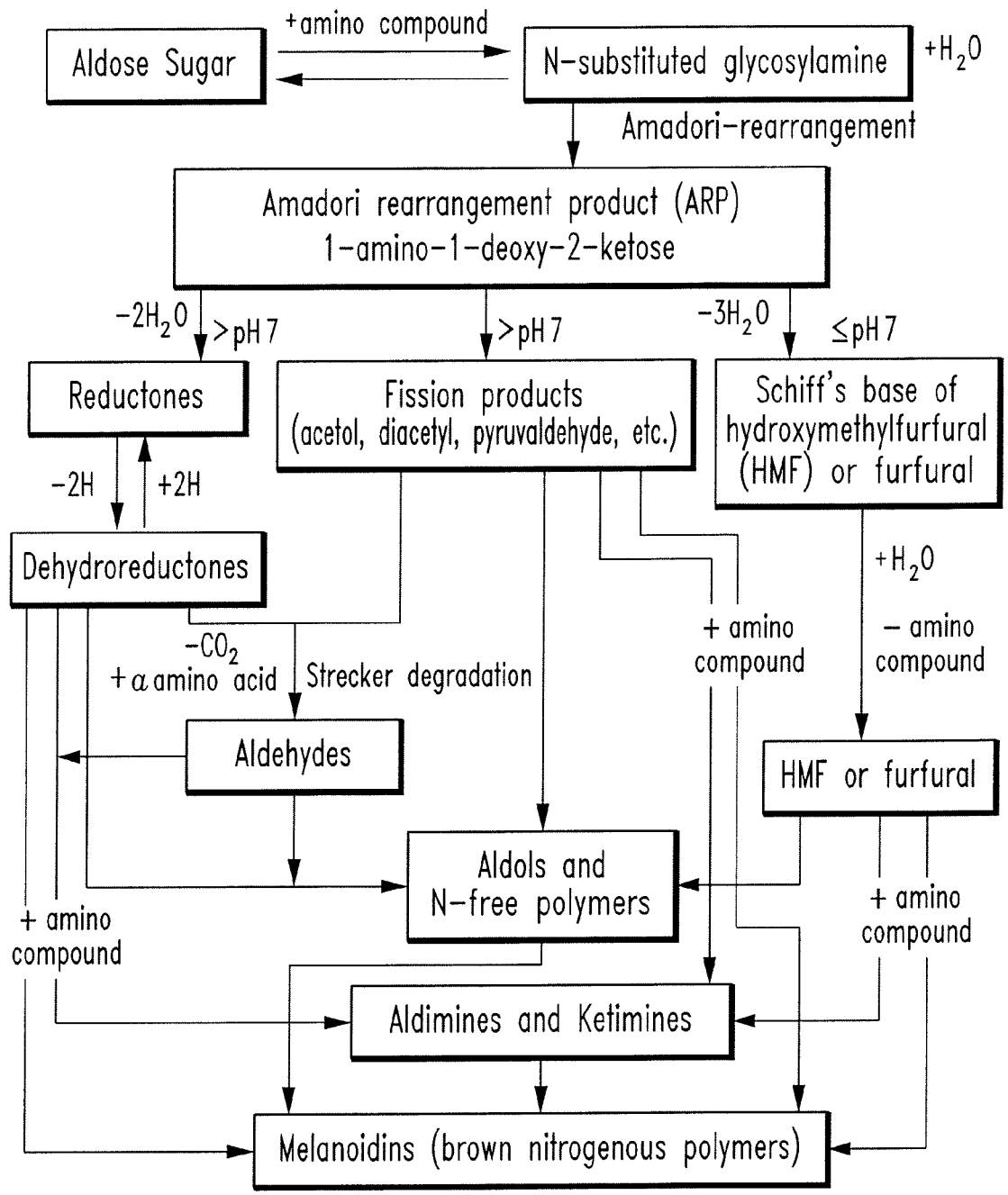
FIG. 2 illustrates a Maillard reaction schematic when reacting a reducing sugar with an amino compound.

FIG. 2 shows a schematic of a Maillard reaction, which culminates in the production of melanoidins. In its initial phase, a Maillard reaction involves a carbohydrate reactant, for example, a reducing sugar (note that the carbohydrate reactant may come from a substance capable of producing a reducing sugar under Maillard reaction conditions). The reaction also involves condensing the carbohydrate reactant (e.g., reducing sugar) with an amine reactant, i.e., a compound possessing an amino group. In other words, the carbohydrate reactant and the amine reactant are the melanoidin reactants for a Maillard reaction. The condensation of these two constituents produces an N-substituted glycosylamine. For a more detailed description of the Maillard reaction see, Hodge, J. E. Chemistry of Browning Reactions in Model Systems *J. Agric. Food Chem.* 1953, 1, 928-943, the disclosure of which is hereby incorporated herein by reference. The compound possessing a free amino group in a Maillard reaction may be present in the form of an amino acid. The free amino group can also come from a protein where the free amino groups are available in the form of, for example, the ε-amino group of lysine residues, and/or the α-amino group of the terminal amino acid.

Another aspect of conducting a Maillard reaction as described herein is that, initially, the aqueous Maillard reactant solution (which also is a binder), as described above, has an alkaline pH. However, once the solution is disposed on a collection of non or loosely assembled matter, and curing is initiated, the pH decreases (i.e., the binder becomes acidic). It should be understood that when fabricating a material, the amount of contact between the binder and components of machinery used in the fabrication is greater prior to curing, (i.e., when the binder solution is alkaline) as compared to after the binder is cured (i.e. when the binder is acidic). An alkaline composition is less corrosive than an acidic composition. Accordingly, corrosivity of the fabrication process is decreased.

It should be appreciated that by using the aqueous Maillard reactant solution described herein, the machinery used to fabricate fiberglass is not exposed as much to an acidic solution because, as described above, the pH of the Maillard reactant solution is alkaline. Furthermore, during the fabrication the only time an acidic condition develops is after the binder has been applied to glass fibers. Once the binder is applied to the glass fibers, the binder and the material that incorporates the binder, has relatively infrequent contacts with the components of the machinery as compared to the time prior to applying the binder to the glass fibers. Accordingly, corrosivity of fiberglass fabrication (and the fabrication of other materials) is decreased.

Figure 4:
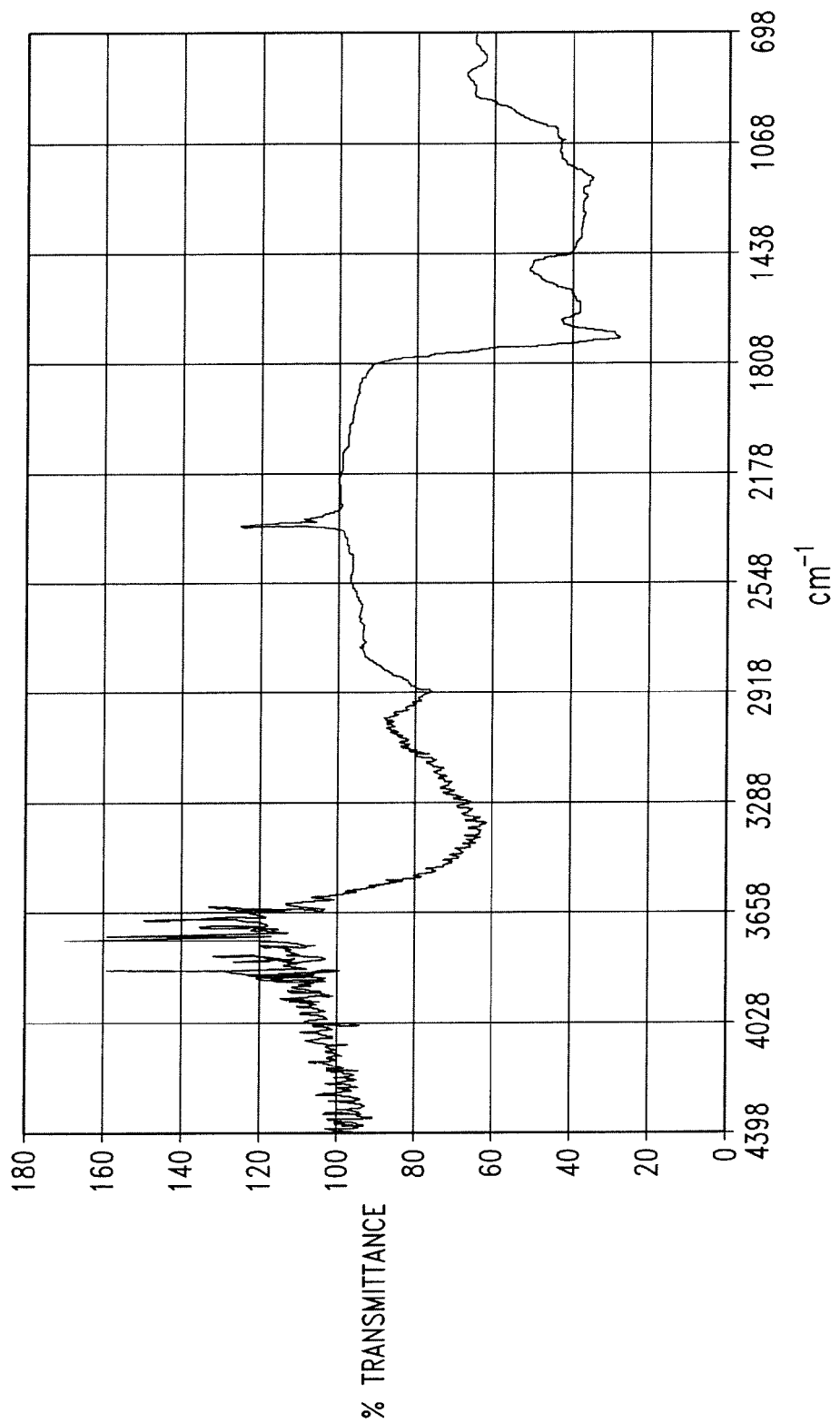
FIG. 4 shows the FT-IR spectrum of an illustrative embodiment of a cured binder of the present disclosure.

Without being bound to theory, covalent reaction of the polycarboxylic acid ammonium salt and reducing sugar reactants of a Maillard reaction, which as described herein occurs substantially during thermal curing to produce brown-colored nitrogenous polymeric and co-polymeric melanoidins of varying structure, is thought to involve initial Maillard reaction of ammonia with the aldehyde moiety of a reducing-sugar carbohydrate reactant to afford N-substituted glycosylamine, as shown in FIG. 2. Consumption of ammonia in such a way, with ammonia and a reducing-sugar carbohydrate reactant combination functioning as a latent acid catalyst, would be expected to result in a decrease in pH, which decrease is believed to promote esterification processes and/or dehydration of the polycarboxylic acid to afford its corresponding anhydride derivative. At pH$\leq$7, the Amadori rearrangement product of N-substituted glycosylamine, i.e., 1-amino-1-deoxy-2-ketose, would be expected to undergo mainly 1,2-enolization with the formation of furfural when, for example, pentoses are involved, or hydroxymethylfurfural when, for example, hexoses are involved, as a prelude to melanoidin production. Concurrently, contemporaneously, or sequentially with the production of melanoidins, esterification processes may occur involving melanoidins, polycarboxylic acid and/or its corresponding anhydride derivative, and residual carbohydrate, which processes lead to extensive cross-linking. Accompanied by sugar dehydration reactions, whereupon conjugated double bonds are produced that may undergo polymerization, a water-resistant thermoset binder is produced consisting of polyester adducts interconnected by a network of carbon-carbon single bonds. Consistent with the above reaction scenario is a strong absorbance near 1734 $cm^{-1}$ in the FT-IR spectrum of a cured binder described herein, which absorbance is within the 1750-1730 $cm^{-1}$ range expected for ester carbonyl C—O vibrations. The afore-mentioned spectrum is shown in FIG. 4.

The following discussion is directed to (i) examples of carbohydrate and amine reactants, which can be used in a Maillard reaction and (ii) how these reactants can be combined. First, it should be understood that any carbohydrate and/or compound possessing a primary or secondary amino group, that will act as a reactant in a Maillard reaction, can be utilized in the binders of the present invention. Such compounds can be identified and utilized by one of ordinary skill in the art with the guidelines disclosed herein.

With respect to exemplary reactants, it should also be appreciated that using an ammonium salt of a polycarboxylic acid as an amine reactant is an effective reactant in a Maillard reaction. Ammonium salts of polycarboxylic acids can be generated by neutralizing the acid groups with an amine base, thereby producing polycarboxylic acid ammonium salt groups. Complete neutralization, i.e., about 100% calculated on an equivalents basis, may eliminate any need to titrate or partially neutralize acid groups in the polycarboxylic acid(s) prior to binder formation. However, it is expected that less-than-complete neutralization would not inhibit formation of the binder. Note that neutralization of the acid groups of the polycarboxylic acid(s) may be carried out either before or after the polycarboxylic acid(s) is mixed with the carbohydrate(s).

With respect to the carbohydrate reactant, it may include one or more reactants having one or more reducing sugars. In one aspect, any carbohydrate reactant should be sufficiently nonvolatile to maximize its ability to remain available for reaction with the polycarboxylic acid ammonium salt reactant. The carbohydrate reactant may be a monosaccharide in its aldose or ketose form, including a triose, a tetrose, a pentose, a hexose, or a heptose; or a polysaccharide; or combinations thereof. A carbohydrate reactant may be a reducing sugar, or one that yields one or more reducing sugars in situ under thermal curing conditions. For example, when a triose serves as the carbohydrate reactant, or is used in combination with other reducing sugars and/or a polysaccharide, an aldotriose sugar or a ketotriose sugar may be utilized, such as glyceraldehyde and dihydroxyacetone, respectively. When a tetrose serves as the carbohydrate reactant, or is used in combination with other reducing sugars and/or a polysaccharide, aldotetrose sugars, such as erythrose and threose; and ketotetrose sugars, such as erythrulose, may be utilized. When a pentose serves as the carbohydrate reactant, or is used in combination with other reducing sugars and/or a polysaccharide, aldopentose sugars, such as ribose, arabinose, xylose, and lyxose; and ketopentose sugars, such as ribulose, arabulose, xylulose, and lyxulose, may be utilized. When a hexose serves as the carbohydrate reactant, or is used in combination with other reducing sugars and/or a polysaccharide, aldohexose sugars, such as glucose (i.e., dextrose), mannose, galactose, allose, altrose, talose, gulose, and idose; and ketohexose sugars, such as fructose, psicose, sorbose and tagatose, may be utilized. When a heptose serves as the carbohydrate reactant, or is used in combination with other reducing sugars and/or a polysaccharide, a ketoheptose sugar such as sedoheptulose may be utilized. Other stereoisomers of such carbohydrate reactants not known to occur naturally are also contemplated to be useful in preparing the binder compositions as described herein. When a polysaccharide serves as the carbohydrate, or is used in combination with monosaccharides, sucrose, lactose, maltose, starch, and cellulose may be utilized.

Furthermore, the carbohydrate reactant in the Maillard reaction may be used in combination with a non-carbohydrate polyhydroxy reactant. Examples of non-carbohydrate polyhydroxy reactants which can be used in combination with the carbohydrate reactant include, but are not limited to, trimethylolpropane, glycerol, pentaerythritol, polyvinyl alcohol, partially hydrolyzed polyvinyl acetate, fully hydrolyzed polyvinyl acetate, and mixtures thereof. In one aspect, the non-carbohydrate polyhydroxy reactant is sufficiently non-volatile to maximize its ability to remain available for reaction with a monomeric or polymeric polycarboxylic acid reactant. It is appreciated that the hydrophobicity of the non-carbohydrate polyhydroxy reactant may be a factor in determining the physical properties of a binder prepared as described herein.

When a partially hydrolyzed polyvinyl acetate serves as a non-carbohydrate polyhydroxy reactant, a commercially available compound such as an 87-89% hydrolyzed polyvinyl acetate may be utilized, such as, DuPont ELVANOL 51-05. DuPont ELVANOL 51-05 has a molecular weight of about 22,000-26,000 Da and a viscosity of about 5.0-6.0 centipoises. Other partially hydrolyzed polyvinyl acetates contemplated to be useful in preparing binder compositions as described herein include, but are not limited to, 87-89% hydrolyzed polyvinyl acetates differing in molecular weight and viscosity from ELVANOL 51-05, such as, for example, DuPont ELVANOL 51-04, ELVANOL 51-08, ELVANOL 50-14, ELVANOL 52-22, ELVANOL 50-26, ELVANOL 50-42; and partially hydrolyzed polyvinyl acetates differing in molecular weight, viscosity, and/or degree of hydrolysis from ELVANOL 51-05, such as, DuPont ELVANOL 51-03 (86-89% hydrolyzed), ELVANOL 70-14 (95.0-97.0% hydrolyzed), ELVANOL 70-27 (95.5-96.5% hydrolyzed), ELVANOL 60-30 (90-93% hydrolyzed). Other partially hydrolyzed polyvinyl acetates contemplated to be useful in preparing binder compositions as described herein include, but are not limited to, Clariant MOWIOL 15-79, MOWIOL 3-83, MOWIOL 4-88, MOWIOL 5-88, MOWIOL 8-88, MOWIOL 18-88, MOWIOL 23-88, MOWIOL 26-88, MOWIOL 40-88, MOWIOL 47-88, and MOWIOL 30-92, as well as Celanese CELVOL 203, CELVOL 205, CELVOL 502, CELVOL 504, CELVOL 513, CELVOL 523, CELVOL 523TV, CELVOL 530, CELVOL 540, CELVOL 540TV, CELVOL 418, CELVOL 425, and CELVOL 443. Also contemplated to be useful are similar or analogous partially hydrolyzed polyvinyl acetates available from other commercial suppliers.

When a fully hydrolyzed polyvinyl acetate serves as a non-carbohydrate polyhydroxy reactant, Clariant MOWIOL 4-98, having a molecular weight of about 27,000 Da, may be utilized. Other fully hydrolyzed polyvinyl acetates contemplated to be useful include, but are not limited to, DuPont ELVANOL 70-03 (98.0-98.8% hydrolyzed), ELVANOL 70-04 (98.0-98.8% hydrolyzed), ELVANOL 70-06 (98.5-99.2% hydrolyzed), ELVANOL 90-50 (99.0-99.8% hydrolyzed), ELVANOL 70-20 (98.5-99.2% hydrolyzed), ELVANOL 70-30 (98.5-99.2% hydrolyzed), ELVANOL 71-30 (99.0-99.8% hydrolyzed), ELVANOL 70-62 (98.4-99.8% hydrolyzed), ELVANOL 70-63 (98.5-99.2% hydrolyzed), ELVANOL 70-75 (98.5-99.2% hydrolyzed), Clariant MOWIOL 3-98, MOWIOL 6-98, MOWIOL 10-98, MOWIOL 20-98, MOWIOL 56-98, MOWIOL 28-99, and Celanese CELVOL 103, CELVOL 107, CELVOL 305, CELVOL 310, CELVOL 325, CELVOL 325LA, and CELVOL 350, as well as similar or analogous fully hydrolyzed polyvinyl acetates from other commercial suppliers.

The aforementioned Maillard reactants may be combined to make an aqueous composition that includes a carbohydrate reactant and an amine reactant. These aqueous binders represent examples of uncured binders. As discussed below, these aqueous compositions can be used as binders of the present invention. These binders are formaldehyde-free, curable, alkaline, aqueous binder compositions. Furthermore, as indicated above, the carbohydrate reactant of the Maillard reactants may be used in combination with a non-carbohydrate polyhydroxy reactant. Accordingly, any time the carbohydrate reactant is mentioned it should be understood that it can be used in combination with a non-carbohydrate polyhydroxy reactant.

In one illustrative embodiment, the aqueous solution of Maillard reactants may include (i) an ammonium salt of one or more polycarboxylic acid reactants and (ii) one or more carbohydrate reactants having a reducing sugar. The pH of this solution prior to placing it in contact with the material to be bound can be greater than or equal to about 7. In addition, this solution can have a pH of less than or equal to about 10. The ratio of the number of moles of the polycarboxylic acid reactant(s) to the number of moles of the carbohydrate reactant(s) can be in the range from about 1:4 to about 1:15. In one example, the ratio of the number of moles of the polycarboxylic acid reactant(s) to the number of moles of the carbohydrate reactant(s) in the binder composition is about 1:5. In another example, the ratio of the number of moles of the polycarboxylic acid reactant(s) to the number of moles of the carbohydrate reactant(s) is about 1:6. In yet another example, the ratio of the number of moles of the polycarboxylic acid reactant(s) to the number of moles of the carbohydrate reactant(s) is about 1:7.

As described above, the aqueous binder composition includes (i) an ammonium salt of one or more polycarboxylic acid reactants and (ii) one or more carbohydrate reactants having a reducing sugar. It should be appreciated that when an ammonium salt of a monomeric or a polymeric polycarboxylic acid is used as an amine reactant, the molar equivalents of ammonium ion may or may not be equal to the molar equivalents of acid salt groups present on the polycarboxylic acid. In one illustrative example, an ammonium salt may be monobasic, dibasic, or tribasic when a tricarboxylic acid is used as a polycarboxylic acid reactant. Thus, the molar equivalents of the ammonium ion may be present in an amount less than or about equal to the molar equivalents of acid salt groups present in a polycarboxylic acid. Accordingly, the salt can be monobasic or dibasic when the polycarboxylic acid reactant is a dicarboxylic acid. Further, the molar equivalents of ammonium ion may be present in an amount less than, or about equal to, the molar equivalents of acid salt groups present in a polymeric polycarboxylic acid, and so on and so forth. When a monobasic salt of a dicarboxylic acid is used, or when a dibasic salt of a tricarboxylic acid is used, or when the molar equivalents of ammonium ions are present in an amount less than the molar equivalents of acid salt groups present in a polymeric polycarboxylic acid, the pH of the binder composition may require adjustment to achieve alkalinity.

The uncured, formaldehyde-free, thermally-curable, alkaline, aqueous binder composition can be used to fabricate a number of different materials. In particular, these binders can be used to produce or promote cohesion in non or loosely assembled matter by placing the binder in contact with the matter to be bound. Any number of well known techniques can be employed to place the aqueous binder in contact with the material to be bound. For example, the aqueous binder can be sprayed on (for example during the binding glass fibers) or applied via a roll-coat apparatus.

These aqueous binders can be applied to a mat of glass fibers (e.g., sprayed onto the mat), during production of fiberglass insulation products. Once the aqueous binder is in contact with the glass fibers the residual heat from the glass fibers (note that the glass fibers are made from molten glass and thus contain residual heat) and the flow of air through the fibrous mat will evaporate (i.e., remove) water from the binder. Removing the water leaves the remaining components of the binder on the fibers as a coating of viscous or semi-viscous high-solids liquid. This coating of viscous or semi-viscous high-solids liquid functions as a binder. At this point, the mat has not been cured. In other words, the uncured binder functions to bind the glass fibers in the mat.

Furthermore, it should be understood that the above described aqueous binders can be cured. For example, any of the above described aqueous binders can be disposed (e.g., sprayed) on the material to be bound, and then heated. For example, in the case of making fiberglass insulation products, after the aqueous binder has been applied to the mat, the binder coated mat is transferred to a curing oven. In the curing oven the mat is heated (e.g., from about 300° F. to about 600° F.) and the binder cured. The cured binder is a formaldehyde-free, water-resistant thermoset binder that attaches the glass fibers of the mat together. Note that the drying and thermal curing may occur either sequentially, contemporaneously, or concurrently.

With respect to making binders that are water-insoluble when cured, it should be appreciated that the ratio of the number of molar equivalents of acid salt groups present on the polycarboxylic acid reactant(s) to the number of molar equivalents of hydroxyl groups present on the carbohydrate reactant(s) may be in the range from about 0.04:1 to about 0.15:1. After curing, these formulations result in a water-resistant thermoset binder. In one variation, the number of molar equivalents of hydroxyl groups present on the carbohydrate reactant(s) is about twenty five-fold greater than the number of molar equivalents of acid salt groups present on the polycarboxylic acid reactant(s). In another variation, the number of molar equivalents of hydroxyl groups present on the carbohydrate reactant(s) is about ten-fold greater than the number of molar equivalents of acid salt groups present on the polycarboxylic acid reactant(s). In yet another variation, the number of molar equivalents of hydroxyl groups present on the carbohydrate reactant(s) is about six-fold greater than the number of molar equivalents of acid salt groups present on the polycarboxylic acid reactant(s).

In other embodiments of the invention, a binder that is already cured can disposed on a material to be bound. As indicated above, most cured binders will typically contain water-insoluble melanoidins. Accordingly, these binders will also be water-resistant thermoset binders.

As discussed below, various additives can be incorporated into the binder composition. These additives give the binders of the present invention additional desirable characteristics. For example, the binder may include a silicon-containing coupling agent. Many silicon-containing coupling agents are commercially available from the Dow-Corning Corporation, Petrarch Systems, and by the General Electric Company. Illustratively, the silicon-containing coupling agent includes compounds such as silylethers and alkylsilyl ethers, each of which may be optionally substituted, such as with halogen, alkoxy, amino, and the like. In one variation, the silicon-containing compound is an amino-substituted silane, such as, gamma-aminopropyltriethoxy silane (General Electric Silicones, SILQUEST A-1101; Wilton, Conn.; USA). In another variation, the silicon-containing compound is an amino-substituted silane, for example, aminoethylaminopropyltrimethoxy silane (Dow Z-6020; Dow Chemical, Midland, Mich.; USA). In another variation, the silicon-containing compound is gamma-glycidoxypropyltrimethoxysilane (General Electric Silicones, SILQUEST A-187). In yet another variation, the silicon-containing compound is an n-propylamine silane (Creanova (formerly Huls America) HYDROSIL 2627; Creanova; Somerset, N.J.; U.S.A.).

The silicon-containing coupling agents are typically present in the binder in the range from about 0.1 percent to about 1 percent by weight based upon the dissolved binder solids (i.e., about 0.1 percent to about 1 percent based upon the weight of the solids added to the aqueous solution). In one application, one or more of these silicon-containing compounds can be added to the aqueous uncured binder. The binder is then applied to the material to be bound. Thereafter, the binder may be cured if desired. These silicone containing compounds enhance the ability of the binder to adhere to the matter the binder is disposed on, such as glass fibers. Enhancing the binder's ability to adhere to the matter improves, for example, its ability to produce or promote cohesion in non or loosely assembled substance(s)

A binder that includes a silicone containing coupling agent can be prepared by admixing about 10 to about 50 weight percent aqueous solution of one or more polycarboxylic acid reactants, already neutralized with an amine base or neutralized in situ, with about 10-50 weight percent aqueous solution of one or more carbohydrate reactants having reducing sugar, and an effective amount of a silicon-containing coupling agent. In one variation, one or more polycarboxylic acid reactants and one or more carbohydrate reactants, the latter having reducing sugar, may be combined as solids, mixed with water, and the mixture then treated with aqueous amine base (to neutralize the one or more polycarboxylic acid reactants) and a silicon-containing coupling agent to generate an aqueous solution 10-50 weight percent in each polycarboxylic acid reactant and each carbohydrate reactant.

In another illustrative embodiment, a binder of the present invention may include one or more corrosion inhibitors. These corrosion inhibitors prevent or inhibit the eating or wearing away of a substance, such as, metal caused by chemical decomposition brought about by an acid. When a corrosion inhibitor is included in a binder of the present invention, the binder's corrosivity is decreased as compared to the corrosivity of the binder without the inhibitor present. In one embodiment, these corrosion inhibitors can be utilized to decrease the corrosivity of the glass fiber-containing compositions described herein. Illustratively, corrosion inhibitors include one or more of the following, a dedusting oil, or a monoammonium phosphate, sodium metasilicate pentahydrate, melamine, tin(II)oxalate, and/or methylhydrogen silicone fluid emulsion. When included in a binder of the present invention, corrosion inhibitors are typically present in the binder in the range from about 0.5 percent to about 2 percent by weight based upon the dissolved binder solids.

By following the disclosed guidelines, one of ordinary skill in the art will be able to vary the concentrations of the reactants of the aqueous binder to produce a wide range of binder compositions. In particular, aqueous binder compositions can be formulated to have an alkaline pH. For example, a pH in the range from greater than or equal to about 7 to less than or equal to about 10. Examples of the binder reactants that can be manipulated include (i) the polycarboxylic acid reactant(s), (ii) the amine base, (iii) the carbohydrate reactant(s), (iv) the silicon-containing coupling agent, and (v) the corrosion inhibitor compounds. Having the pH of the aqueous binders (e.g. uncured binders) of the present invention in the alkaline range inhibits the corrosion of materials the binder comes in contact with, such as machines used in the manufacturing process (e.g., in manufacturing fiberglass). Note this is especially true when the corrosivity of acidic binders is compared to binders of the present invention. Accordingly, the "life span" of the machinery increases while the cost of maintaining these machines decreases. Furthermore, standard equipment can be used with the binders of the present invention, rather than having to utilize relatively corrosive resistant machine components that come into contact with acidic binders, such as stainless steel components. Therefore, the binders disclosed herein decrease the cost of manufacturing bound materials.

The following examples illustrate specific embodiments in further detail. These examples are provided for illustrative purposes only and should not be construed as limiting the invention or the inventive concept to any particular physical configuration in any way. For instance, although 25% (weight percent) aqueous solutions each of triammonium citrate and dextrose monohydrate were admixed in EXAMPLE 1 to prepare aqueous binders, it is to be understood that, in variations of the embodiments described herein, the weight percent of the aqueous, polycarboxylic acid ammonium salt reactant solution and the weight percent of the aqueous, reducing-sugar carbohydrate reactant solution may be altered without affecting the nature of the invention described. For example, admixing aqueous solutions of the polycarboxylic acid ammonium salt reactant and the reducing-sugar carbohydrate reactant the weight percents of which fall within the range from about 10-50 weight percent. Further, although aqueous solutions 10-50% (weight percent) in triammonium citrate and dextrose monohydrate dissolved solids were used in EXAMPLES 8-12 to prepare binder/glass fiber compositions, it is to be understood that the weight percent of the aqueous, polycarboxylic acid ammonium salt reactant-containing/reducing-sugar carbohydrate reactant-containing solution may be altered without affecting the nature of the invention described. For example, preparing aqueous solutions including the polycarboxylic acid ammonium salt reactant and the reducing-sugar carbohydrate reactant the weight percents of which fall outside the range of about 10-50 weight percent. In addition, although the following examples include an ammonium, i.e., $^+NH_4$, salt of a polycarboxylic acid as the polycarboxylic acid ammonium salt reactant, it is to be understood that alternative amine reactants may be used without affecting the nature of the invention described, such as, including a primary amine salt or a secondary amine salt of a polycarboxylic acid.

EXAMPLE 1

Preparation of Aqueous Triammonium
Citrate-Dextrose Binders

Aqueous triammonium citrate-dextrose binders were prepared according to the following procedure: Aqueous solutions (25%) of triammonium citrate (81.9 g citric acid, 203.7 g water, and 114.4 g of a 19% percent solution of ammonia) and dextrose monohydrate (50.0 g of dextrose monohydrate in 150.0 g water) were combined at room temperature in the following proportions by volume: 1:24, 1:12, 1:8, 1:6, 1:5, 1:4, and 1:3, where the relative volume of triammonium citrate is listed as "1." For example, 10 mL of aqueous triammonium citrate mixed with 50 mL of aqueous dextrose monohydrate afforded a "1:5" solution, wherein the mass ratio of triammonium citrate to dextrose monohydrate is about 1:5, the molar ratio of triammonium citrate to dextrose monohydrate is about 1:6, and the ratio of the number of molar equivalents of acid salt groups, present on triammonium citrate, to the number of molar equivalents of hydroxyl groups, present on dextrose monohydrate, is about 0.10:1. The resulting solutions were stirred at room temperature for several minutes, at which time 2-g samples were removed and thermally cured as described in Example 2.

EXAMPLE 2

Preparation of Cured Triammonium Citrate-Dextrose
Binder Samples from Aqueous Triammonium
Citrate-Dextrose Binders 2-g samples of each binder, as prepared in Example 1, were placed onto each of three individual 1-g aluminum bake-out pans. Each binder was then subjected to the following three conventional bake-out/cure conditions in pre-heated, thermostatted convection ovens in order to produce the corresponding cured binder sample: 15 minutes at 400° F., 30 minutes at 350° F., and 30 minutes at 300° F.

EXAMPLE 3

Testing/Evaluation of Cured Triammonium
Citrate-Dextrose Binder Samples Produced from
Aqueous Triammonium Citrate-Dextrose Binders Wet strength was determined for each cured triammonium citrate-dextrose binder sample, as prepared in Example 2, by the extent to which a cured binder sample appeared to remain intact and resist dissolution, following addition of water to the aluminum bake-out pan and subsequent standing at room temperature. Wet strength was noted as Dissolved (for no wet strength), Partially Dissolved (for minimal wet strength), Softened (for intermediate wet strength), or Impervious (for high wet strength, water-insoluble). The color of the water resulting from its contact with cured ammonium citrate-dextrose binder samples was also determined. Table 1 below shows illustrative examples of triammonium citrate-dextrose binders prepared according to Example 1, curing conditions therefor according to Example 2, and testing and evaluation results according to Example 3.

EXAMPLE 4

Elemental Analysis of Cured Triammonium
Citrate-Dextrose (1:6) Binder Samples

Elemental analyses for carbon, hydrogen, and nitrogen (i.e., C, H, N) were conducted on 5-g samples of 15% triammonium citrate-dextrose (1:6) binder, prepared as described in Example 1 and cured as described below, which 0.75-g cured samples included a molar ratio of triammonium citrate to dextrose monohydrate of about 1:6. Binder samples were cured as a function of temperature and time as follows: 300° F. for 1 hour; 350° F. for 0.5 hour; and 400° F. for 0.33 hour. Elemental analyses were conducted at Galbraith Laboratories, Inc. in Knoxville, Tenn. As shown in Table 2, elemental analysis revealed an increase in the C:N ratio as a function of increasing temperature over the range from 300° F. to 350° F., which results are consistent with a melanoidin-containing binder having been prepared. Further, an increase in the C:H ratio as a function of increasing temperature is also shown in Table 2, which results are consistent with dehydration, a process known to occur during formation of melanoidins, occurring during binder cure.

EXAMPLE 5

Preparation of Ammonium Polycarboxylate-Sugar
Binders Used to Construct Glass Bead Shell Bones,
Glass Fiber-containing Mats, and Wood Fiber Board
Compositions Aqueous triammonium citrate-dextrose (1:6) binders, which binders were used to construct glass bead shell bones and glass fiber-containing mats, were prepared by the following general procedure: Powdered dextrose monohydrate (915 g) and powdered anhydrous citric acid (152.5 g) were combined in a 1-gallon reaction vessel to which 880 g of distilled water was added. To this mixture were added 265 g of 19% aqueous ammonia with agitation, and agitation was continued for several minutes to achieve complete dissolution of solids. To the resulting solution were added 3.3 g of SILQUEST A-1101 silane to produce a pH ~8-9 solution (using pH paper), which solution contained approximately 50% dissolved dextrose monohydrate and dissolved ammonium citrate solids (as a percentage of total weight of solution); a 2-g sample of this solution, upon thermal curing at 400° F. for 30 minutes, would yield 30% solids (the weight loss being attributed to dehydration during thermoset binder formation). Where a silane other than SILQUEST A-1101 was included in the triammonium citrate-dextrose (1:6) binder, substitutions were made with SILQUEST A-187 Silane, HYDROSIL 2627 Silane, or Z-6020 Silane. When additives were included in the triammonium citrate-dextrose (1:6) binder to produce binder variants, the standard solution was distributed among bottles in 300-g aliquots to which individual additives were then supplied.

Figure 3:
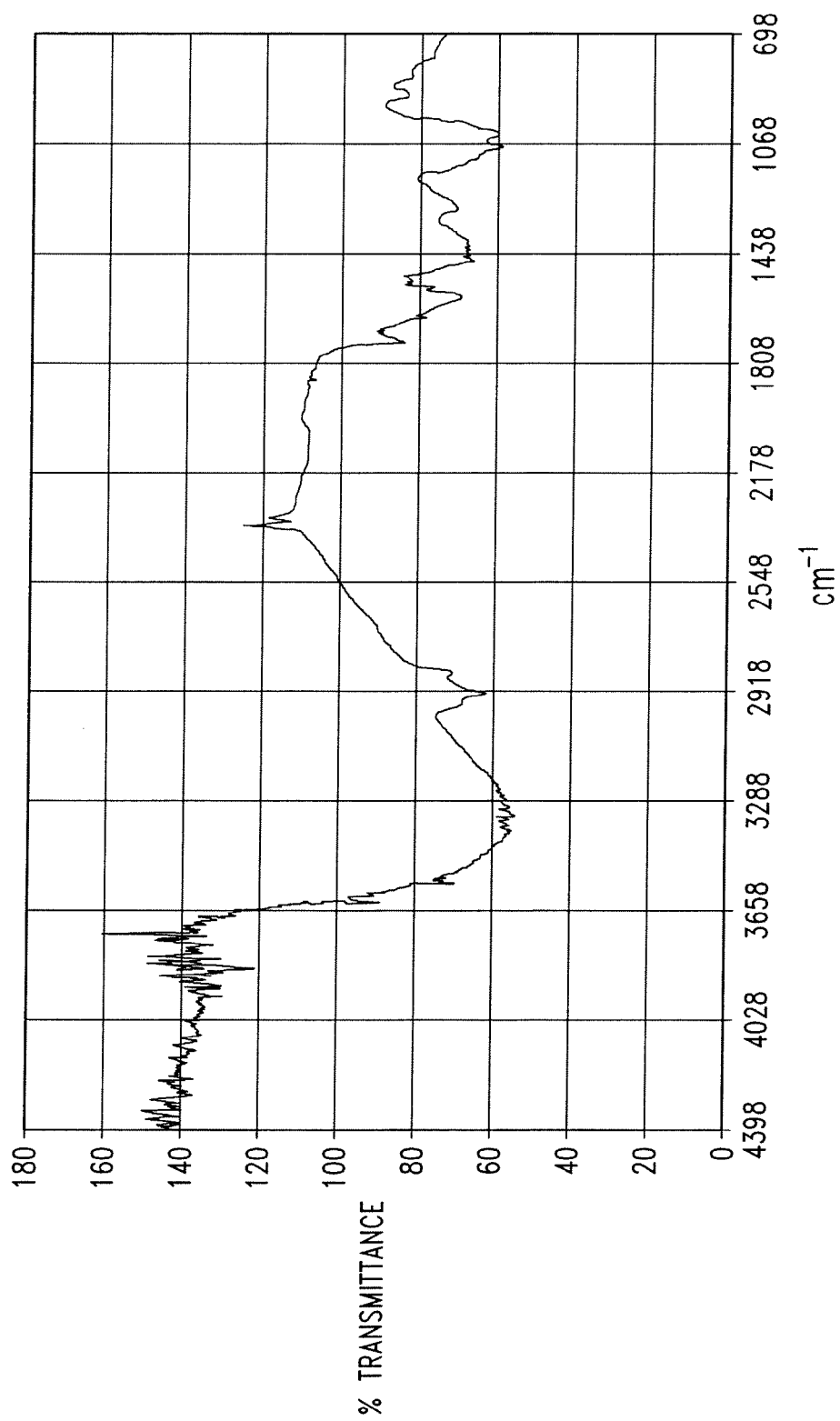
FIG. 3 shows the FT-IR spectrum of an illustrative embodiment of a dried binder of the present disclosure.

The FT-IR spectrum of a dried (uncured) triammonium citrate-dextrose (1:6) binder, which spectrum was obtained as a microscopic thin film from a 10-g sample of a 30% (dissolved binder solids) binder dried in vacuo, is shown in FIG. 3. The FT-IR spectrum of a cured triammonium citrate-dextrose (1:6) Maillard binder, which spectrum was obtained as a microscopic thin film from a 10-g sample of a 30% binder (dissolved binder solids) after curing, is shown in FIG. 4.

When polycarboxylic acids other than citric acid, sugars other than dextrose, and/or additives were used to prepare aqueous ammonium polycarboxylate-sugar binder variants, the same general procedure was used as that described above for preparation of an aqueous triammonium citrate-dextrose (1:6) binder. For ammonium polycarboxylate-sugar binder variants, adjustments were made as necessary to accommodate the inclusion of, for example, a dicarboxylic acid or a polymeric polycarboxylic acid instead of citric acid, or to accommodate the inclusion of, for example, a triose instead of dextrose, or to accommodate the inclusion of, for example, one or more additives. Such adjustments included, for example, adjusting the volume of aqueous ammonia necessary to generate the ammonium salt, adjusting the gram amounts of reactants necessary to achieve a desired molar ratio of ammonium polycarboxylate to sugar, and/or including an additive in a desired weight percent.

EXAMPLE 6

Preparation/Weathering/Testing of Glass Bead Shell Bone Compositions Prepared with Ammonium Polycarboxylate-Sugar Binders When evaluated for their dry and "weathered" tensile strength, glass bead-containing shell bone compositions prepared with a given binder provide an indication of the likely tensile strength and the likely durability, respectively, of fiberglass insulation prepared with that particular binder. Predicted durability is based on a shell bone's weathered tensile strength:dry tensile strength ratio. Shell bones were prepared, weathered, and tested as follows:

Preparation Procedure for Shell Bones:

A shell bone mold (Dietert Foundry Testing Equipment; Heated Shell Curing Accessory, Model 366, and Shell Mold Accessory) was set to a desired temperature, generally 425° F., and allowed to heat up for at least one hour. While the shell bone mold was heating, approximately 100 g of an aqueous ammonium polycarboxylate-sugar binder (generally 30% in binder solids) was prepared as described in Example 5. Using a large glass beaker, 727.5 g of glass beads (Quality Ballotini Impact Beads, Spec. AD, US Sieve 70-140, 106-212 micron-#7, from Potters Industries, Inc.) were weighed by difference. The glass beads were poured into a clean and dry mixing bowl, which bowl was mounted onto an electric mixer stand. Approximately 75 g of aqueous ammonium polycarboxylate-sugar binder were obtained, and the binder then poured slowly into the glass beads in the mixing bowl. The electric mixer was then turned on and the glass beads/ammonium polycarboxylate-sugar binder mixture was agitated for one minute. Using a large spatula, the sides of the whisk (mixer) were scraped to remove any clumps of binder, while also scraping the edges wherein the glass beads lay in the bottom of the bowl. The mixer was then turned back on for an additional minute, then the whisk (mixer) was removed from the unit, followed by removal of the mixing bowl containing the glass beads/ammonium polycarboxylate-sugar binder mixture. Using a large spatula, as much of the binder and glass beads attached to the whisk (mixer) as possible were removed and then stirred into the glass beads/ammonium polycarboxylate-sugar binder mixture in the mixing bowl. The sides of the bowl were then scraped to mix in any excess binder that might have accumulated on the sides. At this point, the glass beads/ammonium polycarboxylate-sugar binder mixture was ready for molding in a shell bone mold.

The slides of the shell bone mold were confirmed to be aligned within the bottom mold platen. Using a large spatula, a glass beads/ammonium polycarboxylate-sugar binder mixture was then quickly added into the three mold cavities within the shell bone mold. The surface of the mixture in each cavity was flattened out, while scraping off the excess mixture to give a uniform surface area to the shell bone. Any inconsistencies or gaps that existed in any of the cavities were filled in with additional glass beads/ammonium polycarboxylate-sugar binder mixture and then flattened out. Once a glass beads/ammonium polycarboxylate-sugar binder mixture was placed into the shell bone cavities, and the mixture was exposed to heat, curing began. As manipulation time can affect test results, e.g., shell bones with two differentially cured layers can be produced, shell bones were prepared consistently and rapidly. With the shell bone mold filled, the top platen was quickly placed onto the bottom platen. At the same time, or quickly thereafter, measurement of curing time was initiated by means of a stopwatch, during which curing the temperature of the bottom platen ranged from about 400° F. to about 430° F., while the temperature of the top platen ranged from about 440° F. to about 470° F. At seven minutes elapsed time, the top platen was removed and the slides pulled out so that all three shell bones could be removed. The freshly made shell bones were then placed on a wire rack, adjacent to the shell bone mold platen, and allowed to cool to room temperature. Thereafter, each shell bone was labeled and placed individually in a plastic storage bag labeled appropriately. If shell bones could not be tested on the day they were prepared, the shell bone-containing plastic bags were placed in a desiccator unit.

Conditioning (Weathering) Procedure for Shell Bones:

A Blue M humidity chamber was turned on and then set to provide weathering conditions of 90° F. and 90% relative humidity (i.e., 90° F./90% rH). The water tank on the side of the humidity chamber was checked and filled regularly, usually each time it was turned on. The humidity chamber was allowed to reach the specified weathering conditions over a period of at least 4 hours, with a day-long equilibration period being typical. Shell bones to be weathered were loaded quickly (since while the doors are open both the humidity and the temperature decrease), one at a time through the open humidity chamber doors, onto the upper, slotted shelf of the humidity chamber. The time that the shell bones were placed in the humidity chamber was noted, and weathering conducted for a period of 24 hours. Thereafter, the humidity chamber doors were opened and one set of shell bones at a time were quickly removed and placed individually into respective plastic storage bags, being sealed completely. Generally, one to four sets of shell bones at a time were weathered as described above. Weathered shell bones were immediately taken to the Instron room and tested.

Test Procedure for Breaking Shell Bones:

In the Instron room, the shell bone test method was loaded on the 5500 R Instron machine while ensuring that the proper load cell was installed (i.e., Static Load Cell 5 kN), and the machine allowed to warm up for fifteen minutes. During this period of time, shell bone testing grips were verified as being installed on the machine. The load cell was zeroed and balanced, and then one set of shell bones was tested at a time as follows: A shell bone was removed from its plastic storage bag and then weighed. The weight (in grams) was then entered into the computer associated with the Instron machine. The measured thickness of the shell bone (in inches) was then entered, as specimen thickness, three times into the computer associated with the Instron machine. A shell bone specimen was then placed into the grips on the Instron machine, and testing initiated via the keypad on the Instron machine. After removing a shell bone specimen, the measured breaking point was entered into the computer associated with the Intron machine, and testing continued until all shell bones in a set were tested.

Test results are shown in Tables 3-6, which results are mean dry tensile strength (psi), mean weathered tensile strength (psi), and weathered:dry tensile strength ratio.

EXAMPLE 7

Preparation/Weathering/Testing of Glass Fiber-Containing Mats Prepared with Ammonium polycarboxylate-Sugar (1:6) Binders When evaluated for their dry and "weathered" tensile strength, glass fiber-containing mats prepared with a given binder provide an indication of the likely tensile strength and the likely durability, respectively, of fiberglass insulation prepared with that particular binder. Predicted durability is based on a glass fiber mat's "weathered" tensile strength:dry tensile strength ratio. Glass fiber mats were prepared, weathered, and tested as follows:

Preparation Procedure for Glass Fiber-Containing Mats:

A "Deckel box," 13 inches high×13 inches wide×14 inches deep, was constructed of clear acrylic sheet and attached to a hinged metal frame. Under the Deckel box, as a transition from the box to a 3-inch drain pipe, was installed a system of a perforated plate and coarse metal screen. A woven plastic belt (called a "wire") was clamped under the Deckel box. For mixing purposes, a 5-gallon bucket equipped with an internal, vertical rib and a high-shear air motor mixer were used. Typically, 4 gallons of water and E-glass (i.e., high-temperature glass) fibers (11 g, 22 g, or 33 g) were mixed for two minutes. A typical E-glass had the following weight percent composition: $SiO_2$, 52.5%; $Na_2O$, 0.3%; CaO, 22.5%; MgO, 1.2%; $Al_2O_3$, 14.5%; $FeO/Fe_2O_3$, 0.2%; $K_2O$, 0.2%; and $B_2O_3$, 8.6%. The drain pipe and transition under the wire had previously been filled with water such that the bottom of the Deckel box was wetted. The aqueous, glass fiber mixture was poured into the Deckel box and agitated vertically with a plate containing forty nine (49) one-inch holes. The slide valve at the bottom of the drain line was opened quickly and the glass fibers collected on the wire. A screen-covered frame, already in place under the wire, facilitated the transfer of the glass fiber sample. The sample was dewatered by passing over an extractor slot with 25-40 inches of water-column suction. One pass was used for a 11-g sample, two passes were used for a 22-g sample, and three passes were used for a 33-g sample. The sample was transferred to a second screen-covered frame and the forming wire removed. The sample was then dried and separated from the screen. Subsequently, the sample was passed over a 3-inch diameter applicator roll rotating in a bath containing an aqueous ammonium polycarboxylate-sugar binder (containing 15% dissolved binder solids, prepared as described in Example 5), wherein the glass fibers were saturated with binder. The excess binder was extracted by passing over the extractor slot again to produce glass fiber-containing mats, which mats were cured at 375° F. for 30 minutes in an oven having up-flow forced convection air.

Conditioning (Weathering) Procedure for Glass Fiber Mats:

Glass fiber-containing mat samples to be conditioned were placed on TEFLON-coated course-weave belt and weighted down to prevent floating. A pair of sample mats were prepared for each ammonium polycarboxylate-sugar binder under evaluation. The mats were conditioned at ambient temperature and humidity in an air-conditioned, but not humidity-controlled room for at least one day. Seven test specimens were cut from each mat using a die with the proper profile; six specimens were cut in one direction and one specimen was cut in a perpendicular direction, with each specimen kept separate. Each specimen was 2 inches wide and narrowed down to 1 inch wide in the mid-section, while being approximately 12 inches long. Three specimens from each mat were placed in a "weathering" chamber at 37-38° C. and 90% relative humidity for 24 hours. The weathered specimens were removed from the chamber and stored in sealable plastic bags, each bag containing a moist paper towel, until immediately before testing.

Test Procedure for Breaking Glass Fiber Mats:

A tensile tester was set up with a crosshead speed of 0.5 inches per minute. The clamp jaws were 2 inches wide and had approximately 1.5-inch grips. Three dry specimens and three weathered specimens were tested from each mat. The dry specimens were used for binder content measurement, as determined by loss on ignition (LOI).

Test results are shown in Table 7, which results are mean % LOI, mean dry tensile strength (lb force), mean weathered tensile strength (lb force), and weathered:dry tensile strength ratio.

EXAMPLE 8

Preparation of Triammonium citrate-Dextrose (1:6) Binder/Glass Fiber Compositions:

Uncured Blanket and Cured Blanket

Powdered dextrose monohydrate (300 lbs) and powdered anhydrous citric acid (50 lbs) were combined in a 260-gallon tote. Soft water was then added to achieve a volume of 235 gallons. To this mixture were added 9.5 gallons of 19% aqueous ammonia, and the resulting mixture was stirred to achieve complete dissolution of solids. To the resulting solution were added 0.56 lbs of SILQUEST A-1101 silane to produce a solution 15.5% in dissolved dextrose monohydrate and dissolved ammonium citrate solids (as a percentage of total weight of solution); a 2-g sample of this solution, upon thermal curing at 400° F. for 30 minutes, would yield 9.3% solids (the weight loss being attributed to dehydration during thermoset binder formation). The solution was stirred for several minutes before being transported to a binder pump where it was used in the manufacture of glass fiber insulation, specifically, in the formation of material referred to as "wet blanket," or uncured blanket, and "amber blanket," or cured blanket.

Uncured blanket and cured blanket were prepared using conventional fiberglass manufacturing procedures; such procedures are described generally below and in U.S. Pat. No. 5,318,990, the disclosure of which is hereby incorporated herein by reference. Typically, a binder is applied to glass fibers as they are being produced and formed into a mat, water is volatilized from the binder, and the high-solids binder-coated fibrous glass mat is heated to cure the binder and thereby produce a finished fibrous glass bat which may be used, for example, as a thermal or acoustical insulation product, a reinforcement for a subsequently produced composite, etc.

A porous mat of fibrous glass was produced by fiberizing molten glass and immediately forming a fibrous glass mat on a moving conveyor. Glass was melted in a tank and supplied to a fiber forming device such as a spinner or a bushing. Fibers of glass were attenuated from the device and then blown generally downwardly within a forming chamber. The glass fibers typically have a diameter from about 2 to about 9 microns and have a length from about 0.25 inch to about 3 inches. Typically, the glass fibers range in diameter from about 3 to about 6 microns, and have a length from about 0.5 inch to about 1.5 inches. The glass fibers were deposited onto a perforated, endless forming conveyor. A binder was applied to the glass fibers, as they were being formed, by means of suitable spray applicators so as to result in a distribution of the binder throughout the formed mat of fibrous glass. The glass fibers, having the uncured binder adhered thereto, were gathered and formed into a mat on the endless conveyor within the forming chamber with the aid of a vacuum drawn through the mat from below the forming conveyor. The residual heat contained in the glass fibers as well as the air flow through the mat caused a majority of the water to volatilize from the mat before it exited the forming chamber. (Water was removed to the extent the uncured binder functioned as a binder; the amount of water to be removed for any particular application can be determined buy one of ordinary skill in the art with routine experimentation)

As the high-solids binder-coated fibrous glass mat emerged from the forming chamber, it expanded vertically due to the resiliency of the glass fibers. The expanded mat was then conveyed to and through a curing oven wherein heated air is passed through the mat to cure the binder. Flights above and below the mat slightly compressed the mat to give the finished product a predetermined thickness and surface finish. Typically, the curing oven was operated at a temperature over a range from about 350° F. to about 600° F. Generally, the mat resided within the oven for a period of time from about 0.5 minute to about 3 minutes. For the manufacture of conventional thermal or acoustical insulation products, the time ranges from about 0.75 minute to about 1.5 minutes. The fibrous glass having a cured, rigid binder matrix emerged from the oven in the form of a bat which may be compressed for packaging and shipping and which will thereafter substantially recover its as-made vertical dimension when unconstrained. By way of example, a fibrous glass mat which is about 1.25 inches thick as it exits from the forming chamber, will expand to a vertical thickness of about 9 inches in the transfer zone, and will be slightly compressed to a vertical thickness of about 6 inches in the curing oven.

Nominal specifications of the cured blanket product prepared as described above were about 0.09 pounds per square foot weight, about 0.7 pounds per cubic foot density, about 1.5 inch thick, fiber diameter of about 22 hundred thousandths of an inch (5.6 microns), about 11% binder content after curing, and about 0.7% mineral oil content for dedusting (dedusting oil). Curing oven temperature was set at about 460° F. Uncured blanket exited the forming chamber white to off-white in apparent color, whereas cured blanket exited the oven dark brown in apparent color and well bonded. After collecting a few rolls of the cured blanket, the matt was broken before the oven, and uncured blanket was also collected for experimentation.

EXAMPLE 9

Preparation of Triammonium Citrate-Dextrose (1:6) Binder/Glass Fiber Composition: Air Duct Board Powdered dextrose monohydrate (1800 lbs) and powdered anhydrous citric acid (300 lbs) were combined in a 2000-gallon mixing tank that contained 743.2 gallons of soft water. To this mixture were added 52.9 gallons of 19% aqueous ammonia under agitation, and agitation was continued for approximately 30 minutes to achieve complete dissolution of solids. To the resulting solution were added 9 lbs of SILQUEST A-1101 silane to produce a pH ~8 solution (using pH paper), which solution contained approximately 25% dissolved dextrose monohydrate and dissolved ammonium citrate solids (as a percentage of total weight of solution); a 2-g sample of this solution, upon thermal curing at 400° F. for 30 minutes, would yield 15% solids (the weight loss being attributed to dehydration during thermoset binder formation). The solution was stirred for several minutes before being transferred to a binder hold tank from which it was used in the manufacture of glass fiber insulation, specifically, in the formation of a product called "air duct board."

Air duct board was prepared using conventional fiberglass manufacturing procedures; such procedures are described generally in Example 8. Nominal specifications of the air duct board product were about 0.4 pounds per square foot density, about 4.5 pounds per cubic foot density, at 1 inch thick, with a fiber diameter of about 32 hundred thousandths of an inch (8.1 microns), and a binder content of about 14.3%, with 0.7% mineral oil for dedusting (dedusting oil). Curing oven temperature was set at about 550° F. Product exited the oven dark brown in apparent color and well bonded.

EXAMPLE 10

Preparation of Triammonium Citrate-Dextrose (1:6) Binder/Glass Fiber Composition: R30 Residential Blanket Powdered dextrose monohydrate (1200 lbs) and powdered anhydrous citric acid (200 lbs) were combined in a 2000-gallon mixing tank that contained 1104 gallons of soft water. To this mixture were added 42.3 gallons of 19% aqueous ammonia under agitation, and agitation was continued for approximately 30 minutes to achieve complete dissolution of solids. To the resulting solution were added 6 lbs of SILQUEST A-1101 silane to produce a pH ~8 solution (using pH paper), which solution contained approximately 13.4% dissolved dextrose monohydrate and dissolved ammonium citrate solids (as a percentage of total weight of solution); a 2-g sample of this solution, upon thermal curing at 400° F. for 30 minutes, would yield 8% solids (the weight loss being attributed to dehydration during thermoset binder formation). The solution was stirred for several minutes before being transferred to a binder hold tank from which it was used in the manufacture of glass fiber insulation, specifically, in the formation of a product called "R30 residential blanket."

R30 residential blanket was prepared using conventional fiberglass manufacturing procedures; such procedures are described generally in Example 8. Nominal specifications of the R30 residential blanket product were about 0.4 pound per square foot weight, a target recovery of 10 inches thick at the end of the line, with a fiber diameter of 18 hundred thousandths of an inch (4.6 microns), 3.8% binder content, and 0.7% mineral oil content for dedusting (dedusting oil). Curing oven temperature was set at about 570° F. Product exited the oven brown in apparent color and well bonded.

EXAMPLE 11

Preparation of Triammonium citrate-Dextrose (1:6) Binder/Glass Fiber Composition: R19 Residential Blanket Batch A-1:

Powdered dextrose monohydrate (1200 lbs) and powdered anhydrous citric acid (200 lbs) were combined in a 2000 gallon mixing tank that contained 1104 gallons of soft water. To this mixture were added 35.3 gallons of 19% ammonia under agitation, and agitation was continued for approximately 30 minutes to achieve complete dissolution of solids. To the resulting solution were added 6 lbs of SILQUEST A-1101 silane to produce a pH ~8 solution (using pH paper), which solution contained about 13.3% dissolved dextrose monohydrate and ammonium citrate solids (as a percentage of total weight of solution); a 2-g sample of this solution, upon thermal curing at 400° F. for 30 minutes, would yield 8% solids (the weight loss being attributed to dehydration during thermoset binder formation). The solution was stirred for several minutes before being transferred to a binder hold tank from which it was used in the manufacture of glass fiber insulation, specifically, in the formation of a product called "R19 Residential Blanket."

R19 Residential Blanket, Batch A-1, was prepared using conventional fiberglass manufacturing procedures; such procedures are described generally in Example 8. Nominal specifications of the R19 Residential Blanket product were about 0.2 pound per square foot weight, 0.2 pound per cubic foot density, a target recovery of 6.5 inches thick at the end of the line, with a fiber diameter of 18 hundred thousandths of an inch (4.6 microns), 3.8% binder content, and 0.7% mineral oil content (for dedusting). Curing oven temperature was set at about 570° F. Product exited the oven brown in apparent color and well bonded.

Batch A-2:

Powdered dextrose monohydrate (1200 lbs) and powdered anhydrous citric acid (200 lbs) were combined in a 2000 gallon mixing tank that contained 558 gallons of soft water. To this mixture were added 35.3 gallons of 19% ammonia under agitation, and agitation was continued for approximately 30 minutes to achieve complete dissolution of solids. To the resulting solution were added 5 lbs of SILQUEST A-1101 silane to produce a pH ~8 solution (using pH paper), which solution contained about 20.5% dissolved dextrose monohydrate and ammonium citrate solids (as a percentage of total weight of solution); a 2-g sample of this solution, upon thermal curing at 400° F. for 30 minutes, would yield 12% solids (the weight loss being attributed to dehydration during thermoset binder formation). The solution was stirred for several minutes before being transferred to a binder hold tank from which it was used in the manufacture of glass fiber insulation, specifically, in the formation of a product called "R19 Residential Blanket."

R19 Residential Blanket, Batch A-2, was prepared using conventional fiberglass manufacturing procedures; such procedures are described generally in Example 8. Nominal specifications of the R19 Residential Blanket product were about 0.2 pound per square foot weight, about 0.4 pound per cubic foot density, a target recovery of 6.5 inches thick at the end of the line, with a fiber diameter of 18 hundred thousandths of an inch (4.6 microns), 3.8% binder content, and 0.7% mineral oil content (for dedusting). Curing oven temperature was set at about 570° F. Product exited the oven brown in apparent color and well bonded.

Batch B:

Powdered dextrose monohydrate (300 lbs) and powdered anhydrous citric acid (50 lbs) were combined in a 260 gallon International Bulk Container (IBC) that already contained 167 gallons of distilled water. To this mixture were added 10.6 gallons of 19% ammonia under agitation, and agitation was continued for approximately 30 minutes to achieve complete dissolution of solids. To the resulting solution were added 1.5 lbs of SILQUEST A-1101 silane to produce a pH ~8 solution (using pH paper), which solution contained approximately 20.1% dissolved dextrose monohydrate and ammonium citrate solids (as a percentage of total weight of solution); a 2-g sample of this solution, upon thermal curing at 400° F. for 30 minutes, would yield 12% solids (the weight loss being attributed to dehydration during thermoset binder formation). The IBC containing the aqueous binder was transferred to an area at which location the binder was pumped into the binder spray rings in the forming hood, diluted thereinto with distilled water, and then used in the manufacture of glass fiber insulation, specifically, in the formation of a product called "R19 Residential Blanket."

R19 Residential Blanket, Batch B, was prepared using conventional fiberglass manufacturing procedures; such procedures are described generally in Example 8. Nominal specifications of the R19 Residential Blanket product made were about 0.2 pound per square foot weight, and about 0.4 pound per cubic foot density, a target recovery of 6.5 inches thick at the end of the line, with a fiber diameter of 18 hundred thousandths of an inch (4.6 microns), 3.8% binder content, and 0.7% mineral oil content (for dedusting). Curing oven temperature was set at about 570° F. Product exited the oven brown in apparent color and well bonded.

Batch C:

Powdered dextrose monohydrate (300 lbs) and powdered anhydrous citric acid (50 lbs) were combined in a 260 gallon International Bulk Container (IBC) that already contained 167 gallons of distilled water. To this mixture were added 10.6 gallons of 19% ammonia under agitation, and agitation was continued for about 30 minutes to achieve complete dissolution of solids. To the resulting solution were added 1.5 lbs of SILQUEST A-1101 silane followed by 1.80 gallons of the methylhydrogen emulsion BS 1040 (manufactured by the Wacker Chemical Corporation) to produce a pH ~8 solution (using pH paper), which solution contained approximately 20.2% dissolved dextrose monohydrate and ammonium citrate solids (as a percentage of total weight of solution); a 2-g sample of this solution, upon thermal curing at 400° F. for 30 minutes, would yield 12% solids (the weight loss being attributed to dehydration during thermoset binder formation). The IBC containing the aqueous binder was transferred to an area at which location the binder was pumped into the binder spray rings in the forming hood, diluted thereinto with distilled water, and then used in the manufacture of glass fiber insulation, specifically, in the formation of a product called "R19 Residential Blanket."

R19 Residential Blanket, Batch C, was prepared using conventional fiberglass manufacturing procedures; such procedures are described generally in Example 8. Nominal specifications of the R19 Residential Blanket product made was about 0.2 pound per square foot density, about 0.4 pound per cubic foot weight, a target recovery of 6.5 inches thick at the end of the line, with a fiber diameter of 18 hundred thousandths of an inch (4.6 microns), 3.8% binder content, and 0.7% mineral oil content (for dedusting). Curing oven temperature was set at about 570° F. Product exited the oven brown in apparent color and well bonded.

Batch D:

Powdered dextrose monohydrate (300 lbs) and powdered anhydrous citric acid (50 lbs) were combined in a 260 gallon International Bulk Container (IBC) that already contained 167 gallons of distilled water. To this mixture were added 10.6 gallons of 19% ammonia under agitation, and agitation was continued for approximately 30 minutes to achieve complete dissolution of solids. To the resulting solution were added 1.5 lbs of SILQUEST A-1101 silane followed by 22 lbs of the clay product Bentalite L10 (manufactured by Southern Clay Products) to produce a pH ~8 solution (using pH paper), which solution contained about 21.0% dissolved dextrose monohydrate and ammonium citrate solids (as a percentage of total weight of solution); a 2-g sample of this solution, upon thermal curing at 400° F. for 30 minutes, would yield 12.6% solids (the weight loss being attributed to dehydration during thermoset binder formation). The IBC containing the aqueous Maillard binder was transferred to an area at which location the binder was pumped into the binder spray rings in the forming hood, diluted thereinto with distilled water, and then used in the manufacture of glass fiber insulation, specifically, in the formation of a product called "R19 Residential Blanket."

R19 Residential Blanket, Batch D, was prepared using conventional fiberglass manufacturing procedures; such procedures are described generally in Example 8. Nominal specifications of the R19 Residential Blanket product made that day were about 0.2 pound per square foot weight, about 0.4 pound per cubic foot density, a target recovery of 6.5 inches thick at the end of the line, with a fiber diameter of 18 hundred thousandths of an inch (4.6 microns), 3.8% binder content, and 0.7% mineral oil content (for dedusting). Curing oven temperature was set at about 570° F. Product exited the oven brown in apparent color and well bonded.

EXAMPLE 12

Preparation of Triammonium citrate-Dextrose (1:6) Binder/Glass Fiber Composition: Pipe Insulation Uncured Powdered dextrose monohydrate (1200 lbs) and powdered anhydrous citric acid (200 lbs) were combined in a 2000-gallon mixing tank that contained 215 gallons of soft water. To this mixture were added 42.3 gallons of 19% aqueous ammonia under agitation, and agitation was continued for approximately 30 minutes to achieve complete dissolution of solids. To the resulting solution were added 6 lbs of SILQUEST A-1101 silane to produce a pH ~8 solution (using pH paper), which solution contained approximately 41.7% dissolved dextrose monohydrate and dissolved ammonium citrate solids (as a percentage of total weight of solution); a 2-g sample of this solution, upon thermal curing at 400° F. for 30 minutes, would yield 25% solids (the weight loss being attributed to dehydration during thermoset binder formation). The solution was stirred for several minutes before being transferred to a binder hold tank from which it was used in the manufacture of glass fiber insulation, specifically, in the formation of a product called "pipe insulation uncured."

Pipe insulation uncured was prepared using conventional fiberglass manufacturing procedures; such procedures are described generally in Example 8. Nominal specifications of the pipe insulation uncured product were about 0.07 pound per square foot weight, about 0.85 pound per cubic foot density, an estimated thickness of 1 inch, a fiber diameter of 30 hundred thousandths of an inch (7.6 microns), and a binder content of 7% when cured. Pipe insulation uncured was transported to a pipe insulation-forming area, where it was cast into cylindrical shells, with 6-inch walls and a 3-inch diameter hole and 4-pound per cubic foot density, to be used as pipe insulation. These shells were cured with the curing oven set at approximately 450° F. to produce dark brown, well-bonded pipe insulation product. Shells cured at higher temperatures exhibited punking and could not be used further for testing.

EXAMPLE 13

Preparation of Triammonium citrate-Dextrose (1:6) Binder/Cellulose Fiber Composition:

Wood Fiber Board

Several methods were used to produce wood fiber boards/sheets bonded with triammonium citrate-dextrose (1:6) binder. A representative method, which method produced strong, uniform samples, is as follows: Wood in the form of assorted pine wood shavings and sawdust was purchased from a local farm supply store. Wood fiber board samples were made with the "as received" wood and also material segregated into the shavings and sawdust components. Wood was first dried in an oven at approximately 200° F. over night, which drying resulted in moisture removal of 14-15% for the wood shavings and about 11% for the sawdust. Thereafter, dried wood was placed in an 8 inch high×12 inch wide×10.5 inch deep plastic container (approximate dimensions). Triammonium citrate-dextrose (1:6) binder was prepared (36% in binder solids) as described in Example 5, and then 160 g of binder was sprayed via an hydraulic nozzle onto a 400-g sample of wood in the plastic container while the container was inclined 30-40 degrees from the vertical and rotated slowly (approximately 5-15 rpm). During this treatment, the wood was gently tumbled while becoming uniformly coated.

Samples of resinated wood were placed in a collapsible frame and compressed in between heated platens under the following conditions: resinated wood shavings, 300 psi; resinated sawdust, 600 psi. For each resinated sample, the cure conditions were 350° F. for 25 to 30 minutes. The resulting sample boards were approximately 10 inches long×10 inches wide, and about 0.4 inches thick before trimming, well-bonded internally, smooth surfaced and made a clean cut when trimmed on the band saw. Trimmed sample density and the size of each trimmed sample board produced were as follows: sample board from wood shavings, density ~54 pcf, size ~8.3 inches long×9 inches wide×0.36 inches thick; sample board from sawdust, density ~44 pcf, size ~8.7 inches long×8.8 inches wide×0.41 inches thick. The estimated binder content of each sample board was ~12.6%.

EXAMPLE 14

Figure 5:
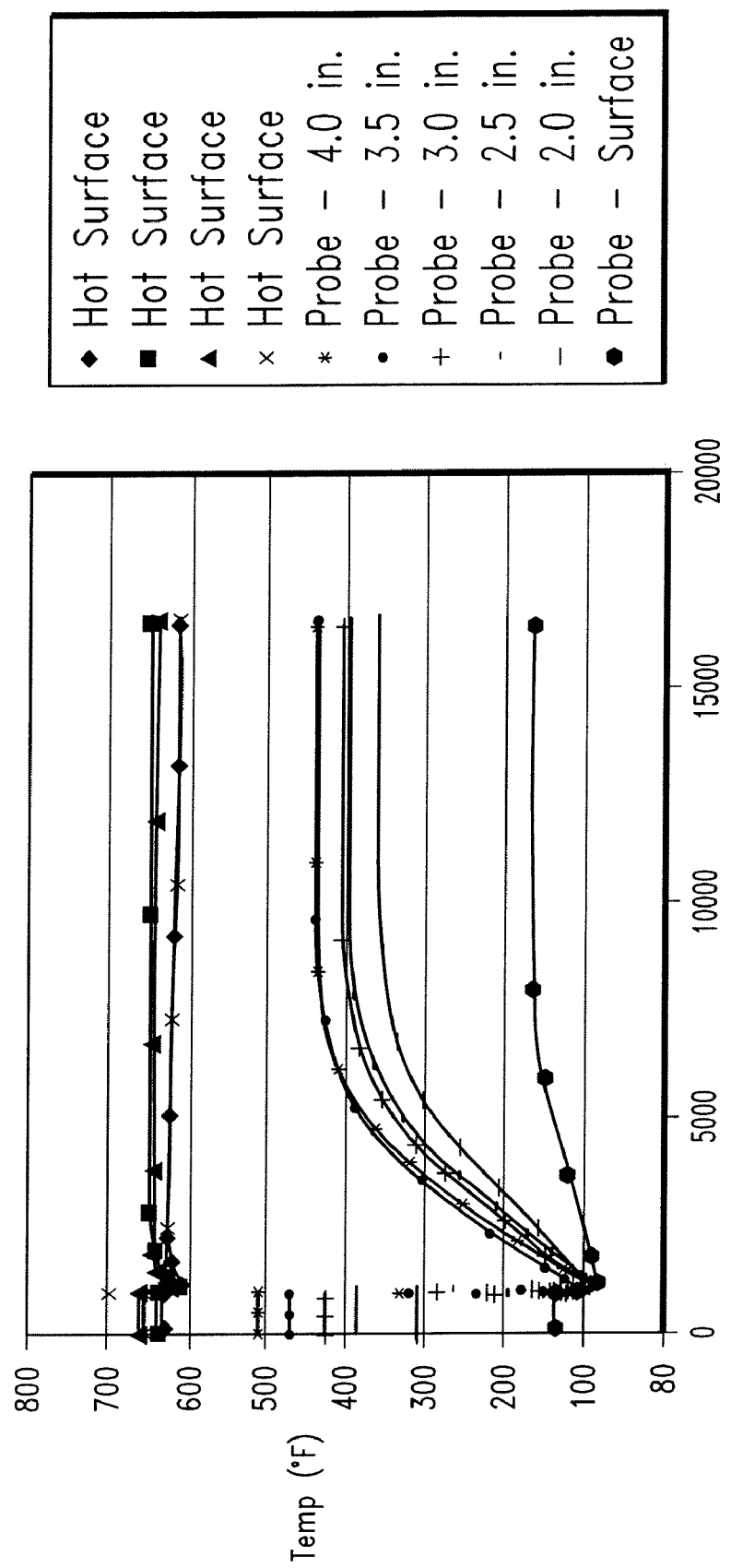
FIG. 5 shows the 650° F. hot surface performance of a fiberglass pipe insulation material fabricated with an illustrative embodiment of a binder of the present disclosure.
Figure 6:
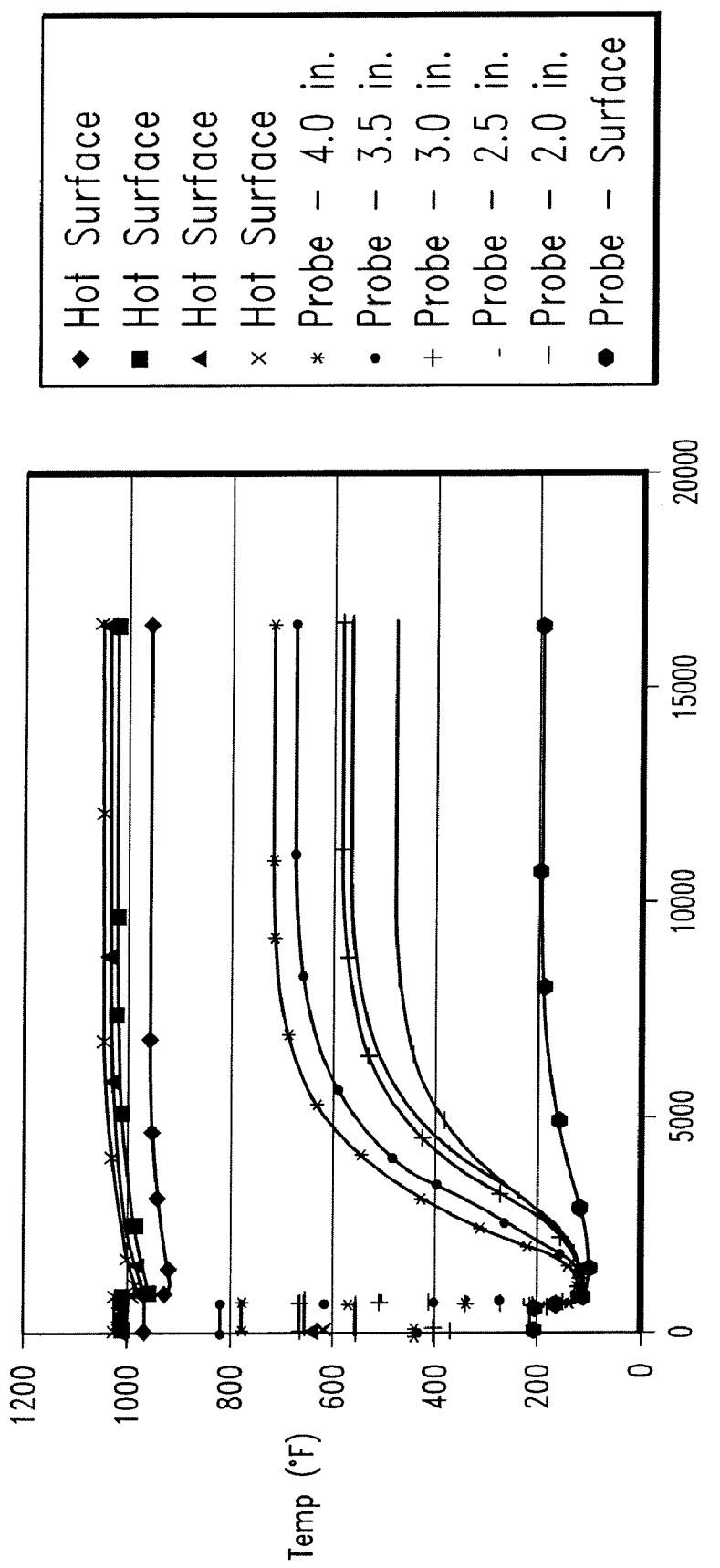
FIG. 6 shows the 1000° F. hot surface performance of a fiberglass pipe insulation material fabricated with an illustrative embodiment of a binder of the present disclosure.

Testing/Evaluation of Triammonium citrate-Dextrose (1:6) Binder/Glass Fiber Compositions The triammonium citrate-dextrose (1:6) binder/glass fiber compositions from Examples 8-12, i.e., cured blanket, air duct board, R30 residential blanket, R19 residential blanket, and pipe insulation uncured, were tested versus a corresponding phenol-formaldehyde (PF) binder/glass fiber composition for one or more of the following: product emissions, density, loss on ignition, thickness recovery, dust, tensile strength, parting strength, durability of parting strength, bond strength, water absorption, hot surface performance, corrosivity on steel, flexural rigidity, stiffness-rigidity, compressive resistance, conditioned compressive resistance, compressive modulus, conditioned compressive modulus, and smoke development on ignition. The results of these tests are shown in Tables 8-13. Also determined were the gaseous compounds produced during pyrolysis of cured blanket from Example 8, and the gaseous compounds produced during thermal curing of pipe insulation uncured from Example 12; these testing results are shown in Tables 14-15. Hot surface performance for cured pipe insulation is shown in FIG. 5 and FIG. 6. Specific tests conducted and conditions for performing these tests are as follows:

Product Emissions Testing

Product emissions for cured blanket from Example 8 and air duct board from Example 9 were determined in accordance with AQS Greenguard Testing procedures. The insulation products were monitored for emissions of total volatile organic compounds (TVOCs), formaldehyde, total selected aldehydes in accordance with ASTM D5116 ("Standard Guide for Small-Scale Environmental Chamber Determinations of Organic Emissions from Indoor Materials/Products"), the United States Environmental Protection Agency (USEPA), and the State of Washington IAQ Specification of January, 1994. The emission data were collected over a one-week exposure period and the resultant air concentrations were determined for each of the aforementioned substances. Air concentration predictions were computer monitored based on the State of Washington requirements, which include a standard room loading and ASHRAE Standard 62-1999 ventilation conditions. Product loading is based on standard wall usage of 28.1 $m^2$ in a 32 $m^3$ room.

Emissions Testing—Selected Aldehydes

The insulation products were tested in a small-sized environmental chamber 0.0855 $m^3$ in volume with the chemical emissions analytically measured. Emission of selected aldehydes, including formaldehyde, were measured following ASTM D5197 ("Standard Test Method for Determination of Formaldehyde and Other Carbonyl Compounds in Air (Active Sampler Methodology)) using high performance liquid chromatography (HPLC). Solid sorbent cartridges with 2,4-dinitrophenylhydrazine (DNPH) were used to collect formaldehyde and other low-molecular weight carbonyl compounds in the chamber air. The DNPH reagent in the cartridge reacted with collected carbonyl compounds to form the stable hydrazone derivatives retained by the cartridge. The hydrazone derivatives were eluted from a cartridge with HPLC-grade acetonitrile. An aliquot of the sample was analyzed for low-molecular weight aldehyde hydrazone derivatives using reverse-phase high-performance liquid chromatography (HPLC) with UV detection. The absorbances of the derivatives were measured at 360 nm. The mass responses of the resulting peaks were determined using multi-point calibration curves prepared from standard solutions of the hydrazone derivatives. Measurements are reported to a quantifiable level of 0.2 ug based on a standard air volume collection of 45 L.

Emissions Testing—Volatile Organic Compounds (VOC)

VOC measurements were made using gas chromatography with mass spectrometric detection (GC/MS). Chamber air was collected onto a solid sorbent which was then thermally desorbed into the GC/MS. The sorbent collection technique, separation, and detection analysis methodology has been adapted from techniques presented by the USEPA and other researchers. The technique follows USEPA Method 1P-1B and is generally applicable to $C_5$-$C_{16}$ organic chemicals with a boiling point ranging from 35° C. to 250° C. Measurements are reported to a quantifiable level of 0.4 ug based on a standard air volume collection of 18 L. Individual VOCs were separated and detected by GC/MS. The total VOC measurements were made by adding all individual VOC responses obtained by the mass spectrometer and calibrating the total mass relative to toluene.

Emissions Testing—Air Concentration Determinations

Emission rates of formaldehyde, total aldehydes, and TVOC were used in a computer exposure model to determine the potential air concentrations of the substances. The computer model used the measured emission rate changes over the one-week time period to determine the change in air concentrations that would accordingly occur. The model measurements were made with the following assumptions: air with open office areas in the building is well-mixed at the breathing level zone of the occupied space; environmental conditions are maintained at 50% relative humidity and 73° F. (23° C.); there are no additional sources of these substances; and there are no sinks or potential re-emitting sources within the space for these substances. The USEPA's Indoor Air Exposure Model, Version 2.0, was specifically modified to accommodate this product and chemicals of interest. Ventilation and occupancy parameters were provided in ASHRAE Standard 62-1999.

Density

The density of cured blanket from Example 8 was determined in accordance with internal test method PTL-1, "Test Method for Density and Thickness of Blanket or Batt Thermal Insulation," which test method is virtually identical to ASTM C 167. The density of air duct board from Example 9 was determined in accordance with internal test method PTL-3, "Test Procedure for Density Preformed Block-Type Thermal Insulation," which test method is virtually identical to ASTM C 303.

Loss on Ignition (LOI)

The loss on ignition for cured blanket from Example 8 and air duct board from Example 9 was determined in accordance with internal test method K-157, "Ignition Loss of Cured Blanket (LOT)." The test was performed on a sample in a wire tray placed in a furnace at 1000° F., +/−50° F., for 15 to 20 minutes to ensure complete oxidation, after which treatment the resulting sample was weighed.

Parting Strength

The parting strength of cured blanket from Example 8, R30 residential blanket from Example 10, and R19 residential blanket from Example 11 were determined in accordance with internal test method KRD-161, which test method is virtually identical to ASTM C 686, "Parting Strength of Mineral Fiber Batt and Blanket-Type Insulation."

Durability of Parting Strength

The durability of parting strength for R30 residential blanket from Example 10 and R19 residential blanket from Example 11 were determined in accordance with ASTM C 686, "Parting Strength of Mineral Fiber Batt and Blanket-Type Insulation," following one-week conditioning at 90° F. and 95% relative humidity.

Tensile Strength

The tensile strength of cured blanket from Example 8 and R19 residential blanket from Example 11 was determined in accordance with an internal test method KRD-161, "Tensile Strength Test Procedure." The test was performed on samples die cut in both the machine direction and the cross-cut machine direction. Samples were conditioned for 24 hours at 75° F. and 50% relative humidity. Ten samples in each machine direction were tested in a test environment of 75° F., 50% relative humidity. The dogbone specimen was as specified in ASTM D638, "Standard Test Method for Tensile Properties of Plastics." A cross-head speed of 2 inches/minute was used for all tests.

Bond Strength

The inter-laminar bond strength of cured blanket from Example 8, R30 residential blanket from Example 10, and R19 residential blanket from Example 11 was determined using an internal test method KRD-159, "Bond Strength of Fiberglass Board and Blanket Products." Molded specimens with a cross sectional area of 6 inches by 6 inches were glued to 6 inch by 7 inch specimen mounting plates and placed in a fixture that applied the force perpendicular to the surface of the specimen. A cross-head speed of 12 inches per minute was used for all tests.

Thickness Recovery

Out-of-package and rollover thickness tests were performed on cured blanket from Example 8 using internal test methods K-123, "Recovered Thickness—End of Line Dead Pin Method—Roll Products," and K-109, "Test Procedure for Recovered Thickness of Roll Products—Rollover Method." Recovered thickness was measured by forcing a pin gauge through a sample of cured blanket from a roll product, either 15 minutes after packaging or at a later point in time, until the pin contacts a flat, hard surface underlying the sample, and then measuring the recovered thickness with a steel rule. Thickness tests were performed on R30 residential blanket from Example 10 and R19 residential blanket from Example 11 using internal test methods K-120, "Test Procedure for Determining End-of-Line Dead-Pin Thickness—Batts," and K-128, "Test Procedure for Recovered Thickness of Batt Products—prop Method," both of which test methods are similar to ASTM C 167, "Standard Test Methods for Thickness and Density of Blanket or Batt Thermal Insulations."

Dust Testing

Dust testing was performed on cured blanket from Example 8, R30 residential blanket from Example 10, and R19 residential blanket from Example 11 using internal test procedure K-102, "Packaged Fiber Glass Dust Test, Batt Method." Dust liberated from randomly selected samples (batts) of cured blanket, R30 residential blanket, and R19 residential blanket dropped into a dust collection box was collected on a filter and the amount of dust determined by difference weighing.

Water Absorption

Water absorption (% by weight) tests were performed on cured blanket from Example 8 and R19 residential blanket from Example 11 using ASTM C 1104, "Test Method for Determining the Water Vapor Absorption of Unfaced Mineral Fiber Insulation."

Flexural Rigidity (EI)

The flexural rigidity of air duct board from Example 9, which is the force couple required to bend the rigid air duct board, i.e., the product of E, the modulus of elasticity, and I, the bending moment of inertia, was determined in accordance with NAIMA AHS 100-74, "Test Method for Flexural Rigidity of Rectangular Rigid Duct Materials."

Stiffness-Rigidity

Stiffness-rigidity testing was performed on R19 residential blanket from Example 11 using internal test procedure K-117, "Test Procedure for Rigidity of Building Insulation." A sample of R19 residential blanket, approximately 47.5 inches in length (±0.5 inch), was placed on the center support bar of a stiffness test apparatus, which apparatus included a protractor scale directly behind the center support bar. With the ends of the sample hanging free, the angle (in degrees) at each end of the sample was recorded by sighting along the bottom edge of the sample while reading the protractor scale.

Compressive Resistance

The compressive resistance of air duct board from Example 9 was determined in accordance with ASTM C 165, "Standard Test Method for Measuring Compressive Properties of Thermal Insulations."

Conditioned Compressive Resistance

The conditioned compressive resistance of air duct board from Example 9, after one week at 90° F. and 95% relative humidity, was determined in accordance with ASTM C 165, "Standard Test Method for Measuring Compressive Properties of Thermal Insulations."

Compressive Modulus

The compressive modulus of air duct board from Example 9 was determined in accordance with ASTM C 165, "Standard Test Method for Measuring Compressive Properties of Thermal Insulations."

Conditioned Compressive Modulus

The conditioned compressive modulus of air duct board from Example 9, after one week at 90° F. and 95% relative humidity, was determined in accordance with ASTM C 165, "Standard Test Method for Measuring Compressive Properties of Thermal Insulations."

Hot Surface Performance

Hot surface performance tests were performed on cured blanket from Example 8, R30 residential blanket from Example 10, and R19 residential blanket from Example 11 using ASTM C 411, "Test Method for Hot Surface Performance of High Temperature Thermal Insulation." Hot surface performance tests were conducted on 3×6-inch sections of cured pipe insulation product from Example 12 at 650° F. and 1000° F. using ASTM C 411, "Test Method for Hot Surface Performance of High Temperature Thermal Insulation." There was no measurable internal temperature rise in the insulation above the pipe hot surface temperature.

Corrosivity on Steel

Corrosivity testing was performed on R30 residential blanket from Example 10 and R19 residential blanket from Example 11 versus steel coupons using internal test procedure Knauf PTL-14, which is virtually identical to ASTM C 665.

Smoke Development on Ignition

Smoke development on ignition for cured blanket from Example 8, with calculation of specific extinction area (SEA), was determined by cone calorimetry using ASTM E 1354, "Test Method for Heat and Visible Smoke Release Rates for Materials and Products Using an Oxygen Consumption Calorimeter."

Gaseous Compounds Produced During Pyrolysis

Gaseous compounds producing during pyrolysis of cured blanket from Example 8 were determined as follows: Approximately 10 g of cured blanket was placed in a test tube, which tube was then heated to 1000° F. for 2.5 minutes at which time the headspace was sampled and analyzed by gas chromatography/mass spectrometry (GC/MS) under the following conditions: Oven, 50° C. for one minute—10° C./minute to 300° C. for 10 minutes; Inlet, 280° C. splitless; Column, HP-5 30 mm×0.32 mm×0.25 um; Column flow, 1.11 mL/minute Helium; Detector, MSD 280° C.; Injection volume, 1 mL; Detector mode, scan 34-700 amu; Threshold, 50; and Sampling Rate, 22 scans/second. A computer search of the mass spectrum of a chromatographic peak in the sample was made against the Wiley library of mass spectra. The best match was reported. A quality index (closeness of match to the library spectra) ranging from 0 to 99 was generated. Only the identity of peaks with a quality index of greater than or equal to 90 were reported.

Gaseous Compounds Produced During Thermal Curing

Gaseous compounds producing during thermal curing of pipe insulation uncured from Example 12 were determined as follows: Approximately 0.6 g of pipe insulation uncured was placed in a test tube, which tube was then heated to 540° F. for 2.5 minutes at which time the headspace was sampled and analyzed by gas chromatography/mass spectrometry under the following conditions: Oven, 50° C. for one minute—10° C./minute to 300° C. for 10 minutes; Inlet, 280° C. splitless; Column, HP-5 30 mm×0.32 mm×0.25 um; Column flow, 1.11 mL/minute Helium; Detector, MSD 280° C.; Injection volume, 1 mL; Detector mode, scan 34-700 amu; Threshold, 50; and Sampling Rate, 22 scans/second. A computer search of the mass spectrum of a chromatographic peak in the sample was made against the Wiley library of mass spectra. The best match was reported. A quality index (closeness of match to the library spectra) ranging from 0 to 99 was generated. Only the identity of peaks with a quality index of greater than or equal to 90 were reported.

TABLE 1

Testing/Evaluation Results for Cured Triammonium citrate-Dextrose Binder Samples[a]

| BINDER COMPOSITION Triammonium citrate[b]:Dextrose•H$_2$O[c] | | | Wet Strength | Water Color | Wet Strength | Water Color | Wet Strength | Water Color |
|---|---|---|---|---|---|---|---|---|
| Mass Ratio | Mole Ratio[d] | COOH:OH Ratio[d] | (400° F.) | (400° F.) | (350° F.) | (350° F.) | (300° F.) | (300° F.) |
| 1:24 | (1:30) | 0.02:1 | Dissolved | Light caramel-colored | Dissolved | Light caramel-colored | Dissolved | Light caramel-colored |
| 1:12 | (1:15) | 0.04:1 | Impervious | Clear and colorless | Dissolved | Caramel-colored | Dissolved | Caramel-colored |
| 1:8 | (1:10) | 0.06:1 | Impervious | Clear and colorless | Partially Dissolved | Caramel-colored | Dissolved | Caramel-colored |
| 1:6 | (1:7) | 0.08:1 | Impervious | Clear and colorless | Softened | Clear yellow | Dissolved | Caramel-colored |
| 1:5 | (1:6) | 0.10:1 | Impervious | Clear and colorless | Softened | Clear yellow | Dissolved | Caramel-colored |
| 1:4[e] | (1:5)[e] | 0.12:1[e] | Impervious | Clear and colorless | Softened | Clear yellow | Dissolved | Caramel-colored |
| 1:3[e] | (1:4)[e] | 0.15:1[e] | Impervious | Clear and colorless | Softened | Clear orange | Dissolved | Caramel-colored |

[a]From Example 1
[b]MW = 243 g/mol; 25% (weight percent) solution
[c]MW = 198 g/mol; 25% (weight percent) solution
[d]Approximate
[e]Associated with distinct ammonia smell

TABLE 2

Elemental Analysis Results for Cured Triammonium Citrate-Dextrose (1:6) Binder Samples[a] as a Function of Temperature and Time

| Cure Temp | Cure Time | Elemental Analysis | Elemental Analysis Results | | C:H | C:N |
|---|---|---|---|---|---|---|
| 300° F. | 1 hour | Carbon Hydrogen Nitrogen | 48.75% 5.60% 4.10% | | 8.70 | 11.89 |
| 300° F. | 1 hour | Carbon Hydrogen Nitrogen | 49.47% 5.55% 4.12% | | 8.91 | 12.00 |
| 300° F. | 1 hour | Carbon Hydrogen Nitrogen | 50.35% 5.41% 4.18% | Avg. -- | 9.31 8.97 | 12.04 11.98 |
| 350° F. | 0.5 hour | Carbon Hydrogen Nitrogen | 52.55% 5.20% 4.25% | | 10.10 | 12.36 |
| 350° F. | 0.5 hour | Carbon Hydrogen Nitrogen | 54.19% 5.08% 4.40% | | 10.67 | 12.31 |
| 350° F. | 0.5 hour | Carbon Hydrogen Nitrogen | 52.86% 5.17% 4.24% | Avg. -- | 10.22 10.33 | 12.47 12.38 |
| 400° F. | 0.33 hour | Carbon Hydrogen Nitrogen | 54.35% 5.09% 4.45% | | 10.68 | 12.21 |
| 400° F. | 0.33 hour | Carbon Hydrogen Nitrogen | 55.63% 5.06% 4.58% | | 10.99 | 12.15 |
| 400° F. | 0.33 hour | Carbon Hydrogen Nitrogen | 56.10% 4.89% 4.65% | Avg. -- | 11.47 11.05 | 12.06 12.14 |

[a]From Example 4

TABLE 3

Measured Tensile Strength for Glass Bead Shell Bone Compositions[a] Prepared With Triammonium Citrate-Dextrose (1:6) Binder[b] vs. Standard PF Binder

| Binder Description | Weathered:Dry Tensile Strength Ratio | Mean[c] Dry Tensile Strength (psi) | Mean[c] Weathered Tensile Strength (psi) |
|---|---|---|---|
| Triammonium Citrate-Dextrose[d] | 0.71 | 286 | 202 |
| Triammonium Citrate-Dextrose[d] | 0.76 | 368 | 281 |
| Triammonium Citrate-Dextrose[d] | 0.79 | 345 | 271 |
| Triammonium Citrate-Dextrose[d] | 0.77 | 333 | 256 |
| Triammonium Citrate-Dextrose[d] | 0.82 | 345 | 284 |
| Triammonium Citrate-Dextrose[d] | 0.75 | 379 | 286 |
| Triammonium Citrate-Dextrose[d] | 0.74 | 447 | 330 |
| Triammonium Citrate-Dextrose[e] | 0.76[e] | 358[e] | 273[e] |
| Triammonium Citrate-Dextrose: | | | |
| Day Binder Made | 0.79 | 345 | 271 |
| 1 Day After Binder Made | 0.76 | 352 | 266 |
| 2 Day After Binder Made | 0.72 | 379 | 272 |

TABLE 3-continued

Measured Tensile Strength for Glass Bead Shell Bone Compositions[a] Prepared With Triammonium Citrate-Dextrose (1:6) Binder[b] vs. Standard PF Binder

| Binder Description | Weathered:Dry Tensile Strength Ratio | Mean[c] Dry Tensile Strength (psi) | Mean[c] Weathered Tensile Strength (psi) |
|---|---|---|---|
| 1 Week After Binder Made | 0.88 | 361 | 316 |
| 2 Weeks After Binder Made | 0.82 | 342 | 280 |
| Triammonium citrate-Dextrose with Silane Substitution: | | | |
| SILQUEST A-187 silane substituted 1:1 by weight for SILQUEST A-1101 | 0.69 | 324 | 222 |
| SILQUEST A-187 silane substituted 2:1 by weight for SILQUEST A-1101 | 0.71 | 351 | 250 |
| HYDROSIL 2627 silane substituted 1:1 by weight for SILQUEST A-1101 | 0.87 | 337 | 293 |
| HYDROSIL 2627 silane substituted 2:1 by weight for SILQUEST A-1101 | 0.99 | 316 | 312 |
| Z-6020 silane substituted 1:1 by weight for SILQUEST A-1101 | 0.78 | 357 | 279 |
| Z-6020 silane substituted 2:1 by weight for SILQUEST A-1101 | 0.78 | 373 | 291 |
| Standard PF (Ductliner) Binder | 0.79 | 637 | 505 |

[a]From Example 6
[b]From Example 5
[c]Mean of nine shell bone samples
[d]One of seven different batches of triammonium citrate-dextrose (1:6) binder made over a five-month period
[e]Average of seven different batches of triammonium citrate-dextrose (1:6) binder made over a five-month period

TABLE 4

Measured Tensile Strength for Glass Bead Shell Bone Compositions[a] Prepared With Triammonium Citrate-Dextrose (1:6) Binder Variants[b] vs. Standard PF Binder

| Binder Description | Quantity of Additive in 300 g of binder (grams) | Weathered:Dry Tensile Strength Ratio | Mean[c] Dry Tensile Strength (psi) | Mean[c] Weathered Tensile Strength (psi) |
|---|---|---|---|---|
| Triammonium citrate-Dextrose[d] | — | 0.76[d] | 358[d] | 273[d] |
| Triammonium citrate-Dextrose with Additive: | | | | |
| Silres BS 1042[e] | 1.6 | 0.84 | 381 | 325 |
| Silres BS 1042 | 3.2 | 0.94 | 388 | 363 |
| Silres BS 1042 | 4.8 | 1.01 | 358 | 362 |
| Sodium Carbonate | 0.45 | 0.88 | 281 | 248 |
| Sodium Carbonate | 0.9 | 0.71 | 339 | 242 |
| Sodium Carbonate | 1.35 | 0.89 | 282 | 251 |
| Silres BS 1042 + Sodium Carbonate | 1.6 + 1.35 | 0.84 | 335 | 280 |
| Silres BS 1042 + Sodium Carbonate | 3.2 + 0.9 | 0.93 | 299 | 277 |
| Silres BS 1042 + Sodium Carbonate | 4.8 + 0.48 | 0.73 | 368 | 270 |
| Sodium Carbonate[f] | 0.9 | 0.83 | 211 | 175 |
| Sodium Carbonate[f] | 0.9 | 0.69 | 387 | 266 |
| Sodium Carbonate | 1.8 | 0.81 | 222 | 180 |
| Sodium Carbonate[g] | 1.8 | 0.66 | 394 | 259 |
| LE 46[h] | 6.4 | 0.80 | 309 | 248 |
| LE 46 | 12.9 | 0.98 | 261 | 256 |
| TPX5688/AQUA-TRETE BSM40[i] | 5.6 | 0.78 | 320 | 250 |
| Silres BS 1042 | 6.4 | 0.91 | 308 | 280 |
| Trimethylmethoxysilane | 0.9 | 0.78 | 262 | 205 |
| Potassium Permanganate | 0.2 | 0.69 | 302 | 207 |
| PGN[j] | 9 | 0.82 | 246 | 201 |
| Cloisite NA+[k] | 9 | 0.71 | 280 | 199 |
| Blown Soya Emulsion (25%)[l] | 18 | 1.04 | 239 | 248 |
| Flaxseed Oil Emulsion (25%) | 18 | 0.90 | 362 | 326 |
| Bentolite L-10[m] | 9 | 1.00 | 288 | 288 |
| Michem 45745 PE Emulsion (50%)[n] | 9 | 0.81 | 335 | 270 |
| Bone Glue Solution[o] | 15 | 0.82 | 435 | 358 |

TABLE 4-continued

Measured Tensile Strength for Glass Bead Shell Bone Compositions[a] Prepared With
Triammonium Citrate-Dextrose (1:6) Binder Variants[b] vs. Standard PF Binder

| Binder Description | Quantity of Additive in 300 g of binder (grams) | Weathered:Dry Tensile Strength Ratio | Mean[c] Dry Tensile Strength (psi) | Mean[c] Weathered Tensile Strength (psi) |
|---|---|---|---|---|
| Tannic Acid | 4.5 | 0.79 | 474 | 375 |
| Glycine | 4.5 | 0.80 | 346 | 277 |
| Glycerol | 5.28 | 0.69 | 361 | 249 |
| Sodium Tetraborate Decahydrate + Glycerol | 0.9 + 4.5 | 0.74 | 378 | 280 |
| Sodium Tetraborate Decahydrate 1% | 0.9 | 0.86 | 387 | 331 |
| Sodium Tetraborate Decahydrate 2% | 1.8 | 0.80 | 335 | 267 |
| Sodium Tetraborate Decahydrate 3% | 2.5 | 0.84 | 334 | 282 |
| Axel INT-26-LF95[p] | 0.9 | 0.70 | 374 | 263 |
| ISO Chill Whey[q] 1% | 0.9 | 0.74 | 444 | 328 |
| ISO Chill Whey 2% | 1.8 | 1.01 | 407 | 412 |
| ISO Chill Whey 5% | 4.5 | NC[r] | 473 | NM[s] |
| Resorcinol 5% | 4.5 | 0.76 | 331 | 251 |
| Maltitol | 3.23 | 0.82 | 311 | 256 |
| Standard PF (Ductliner) Binder | — | 0.79 | 637 | 505 |

[a]From Example 6
[b]From Example 5
[c]Mean of nine shell bone samples
[d]Average of seven different batches of triammonium citrate-dextrose (1:6) binder made over a five-month period
[e]Silres BS 1042 to be 50% solids emulsion of methylhydrogen polysiloxane
[f]Replicate samples
[g]Replicate sample
[h]LE 46 to be 35% solids emulsion of polydimethylsiloxane
[i]TPX5688/AQUA-TRETE BSM40 to be 40% emulsion of alkylsilane
[j]PGN, a grade of clay, montmorillonite, from Nanocor
[k]Cloisite NA+, the sodium salt of a clay from Southern Clay Products
[l]Blown Soya Emulsion (25%), a 25% solids emulsion of soybean oil with PEG 400 dioleate (4% on solids) and guar gum (1% on solids)
[m]Bentolite L-10, a clay from Southern Clay Products
[n]Michem 45745 PE Emulsion (50%), a 25% solids emulsion of low molecular weight polyethylene
[o]Bone Glue Solution, a 30% solids solution
[p]Axel INT-26-LF95, a fat-based, mold-release agent/emulsion
[q]ISO Chill Whey 9010
[r]Not calculated
[s]Not measured

TABLE 5

Measured Tensile Strength for Glass Bead Shell Bone Compositions[a]
Prepared With Ammonium Polycarboxylate-Dextrose Binder Variants[b]
vs. Polycarboxylic Acid-based Binders vs. Standard PF Binder

| Binder Description | Weathered:Dry Tensile Strength Ratio | Mean[c] Dry Tensile Strength (psi) | Mean[c] Weathered Tensile Strength (psi) |
|---|---|---|---|
| Triammonium citrate-dextrose (1:6)[d] | 0.76[d] | 358[d] | 273[d] |
| Triammonium citrate-dextrose (1:5) | 0.68 | 377 | 257 |
| +Sodium carbonate (0.9 g) | 0.71 | 341 | 243 |
| +Sodium carbonate (1.8 g) | 0.78 | 313 | 243 |
| AQUASET-529 + Dex + Ammonia[e] | 0.41 | 499 | 205 |
| AQUASET-529 + Dex + Silane[f] | 0.57 | 541 | 306 |
| AQUASET-529 + Ammonia + Silane[g] | 0.11 | 314 | 33 |
| AQUASET-529 + Silane[h] | 0.48 | 605 | 293 |
| PETol + Maleic Acid + Silane[i] | 0.73 | 654 | 477 |
| PETol + Maleic Acid + TSA + Silane[j] | 0.64 | 614 | 390 |
| [Binder[j] + Ammonia + Dex + Silane][k] | 0.58 | 420 | 245 |
| PETol + Citric Acid + Silane[l] | 0.56 | 539 | 303 |
| CRITERION 2000 + Glycerol[m] | 0.26 | 532 | 136 |
| CRITERION 2000 + Glycerol[n] | 0.20 | 472 | 95 |
| SOKALAN + Dex + Ammonia[o] | 0.66 | 664 | 437 |

TABLE 5-continued

Measured Tensile Strength for Glass Bead Shell Bone Compositions[a]
Prepared With Ammonium Polycarboxylate-Dextrose Binder Variants[b]
vs. Polycarboxylic Acid-based Binders vs. Standard PF Binder

| Binder Description | Weathered:Dry Tensile Strength Ratio | Mean[c] Dry Tensile Strength (psi) | Mean[c] Weathered Tensile Strength (psi) |
|---|---|---|---|
| NF1 + Dex + Ammonia[p] | 0.50 | 877 | 443 |
| Standard PF (Ductliner) Binder | 0.79 | 637 | 505 |

[a]From Example 6
[b]From Example 5
[c]Mean of nine shell bone samples
[d]Average of seven different batches of triammonium citrate-dextrose (1:6) binder made over a five-month period
[e]200 g AQUASET-529 + 87 g 19% ammonia + 301 g Dextrose + 301 g water to be a 30% solution
[f]300 mL of solution from binder[e] + 0.32 g of SILQUEST A-1101
[g]200 g AQUASET-529 + 87 g 19% ammonia + 101 g water + 0.6 g SILQUEST A-1101
[h]AQUASET-529 + SILQUEST A-1101 (at 0.5% binder solids), diluted to 30% solids
[i]136 g pentaerythritol + 98 g maleic anhydride + 130 g water, refluxed for 30 minutes; 232 g of resulting solution mixed with 170 g water and 0.6 g of SILQUEST A-1101
[j]136 g pentaerythritol + 98 g maleic anhydride + 130 g water + 1.5 mL of 66% p-toluenesulfonic acid, refluxed for 30 minutes; 232 g of resulting solution mixed with 170 g water and 0.6 g of SILQUEST A-1101
[k]220 g of binder[j] + 39 g of 19% ammonia + 135 g Dextrose + 97 g water + 0.65 g SILQUEST A-1101
[l]128 g of citric acid + 45 g of pentaerythritol + 125 g of water, refluxed for 20 minutes; resulting mixture diluted to 30% solids and SILQUEST A-1101 added at 0.5% on solids
[m]200 g of Kemira CRITERION 2000 + 23 g glycerol + 123 g water + 0.5 g SILQUEST A-1101
[n]200 g of Kemira CRITERION 2000 + 30 g glycerol + 164 g water + 0.6 g SILQUEST A-1101
[o]100 g of BASF SOKALAN CP 10 S + 57 g 19% ammonia + 198 g Dextrose + 180 g water + 0.8 g SILQUEST A-1101
[p]211 g of H. B. Fuller NF1 + 93 g 19% ammonia + 321 g Dextrose + 222 g water + 1.33 g SILQUEST A-1101

TABLE 6

Measured Tensile Strength for Glass Bead Shell Bone Compositions[a] Prepared
With Ammonium Polycarboxylate-Sugar Binder Variants[b] vs. Standard PF Binder

| Binder Description | Molar Ratio | Weathered:Dry Tensile Strength Ratio | Mean[c] Dry Tensile Strength (psi) | Mean[c] Weathered Tensile Strength (psi) |
|---|---|---|---|---|
| Triammonium citrate-Dextrose[d] | Dextrose = 2 × COOH | 0.76[d] | 358[d] | 273[d] |
| Triammonium citrate-DHA[e] | DHA = 2 × COOH | 1.02 | 130 | 132 |
| Triammonium citrate-Xylose | Xylose = 2 × COOH | 0.75 | 322 | 241 |
| Triammonium citrate-Fructose | Fructose = 2 × COOH | 0.79 | 363 | 286 |
| Diammonium tartarate-Dextrose | Dextrose = 2 × COOH | 0.76 | 314 | 239 |
| Diammonium maleate-Dextrose | Dextrose = 2 × COOH | 0.78 | 393 | 308 |
| Diammonium maliate-Dextrose | Dextrose = 2 × COOH | 0.67 | 49 | 280 |
| Diammonium succinate-Dextrose | Dextrose = 2 × COOH | 0.70 | 400 | 281 |
| Ammonium lactate[f]-Dextrose | Dextrose = 2 × COOH | 0.68 | 257 | 175 |
| Ammonia + tannic acid[g]-Dextrose | Dextrose = 2 × NH$_4^{+h}$ | 0.50 | 395 | 199 |
| Standard PF (Ductliner) Binder | — | 0.79 | 637 | 505 |

[a]From Example 6
[b]From Example 5
[c]Mean of nine shell bone samples
[d]Average of seven batches
[e]DHA = dihydroxyacetone
[f]Monocarboxylate
[g]Non-carboxylic acid
[h]pH ≥ 7

TABLE 7

Measured Tensile Strength and Loss on Ignition for Glass Fiber Mats[a] Prepared
With Ammonium Polycarboxylate-Sugar (1:6) Binder Variants[b] vs. Standard PF Binder

| Binder Composition | Mean % LOI | Weathered:Dry Tensile Strength Ratio | Mean[c] Dry Tensile Strength (lb force) | Mean[c] Weathered Tensile Strength (lb force) |
|---|---|---|---|---|
| Triammonium citrate-Dex[d] | 5.90 | 0.63 | 11.4 | 7.2 |
| Triammonium citrate-Dex | 6.69 | 0.72 | 14.6 | 10.5 |
| Diammonium maliate-Dex | 5.02 | 0.86 | 10.2 | 8.8 |
| Diammonium maliate-Dex | 6.36 | 0.78 | 10.6 | 8.3 |
| Diammonium succinate-Dex | 5.12 | 0.61 | 8.0 | 4.9 |

TABLE 7-continued

Measured Tensile Strength and Loss on Ignition for Glass Fiber Mats[a] Prepared With Ammonium Polycarboxylate-Sugar (1:6) Binder Variants[b] vs. Standard PF Binder

| Binder Composition | Mean % LOI | Weathered:Dry Tensile Strength Ratio | Mean[c] Dry Tensile Strength (lb force) | Mean[c] Weathered Tensile Strength (lb force) |
|---|---|---|---|---|
| Diammonium succinate-Dex | 4.97 | 0.76 | 7.5 | 5.7 |
| Triammonium citrate-Fruc[e] | 5.80 | 0.57 | 11.9 | 6.8 |
| Triammonium citrate-Fruc | 5.96 | 0.60 | 11.4 | 6.8 |
| Diammonium maliate-Fruc | 6.01 | 0.60 | 9.0 | 5.4 |
| Diammonium maliate-Fruc | 5.74 | 0.71 | 7.9 | 5.6 |
| Diammonium succinate-Fruc | 4.60 | 1.05 | 3.7 | 3.9 |
| Diammonium succinate-Fruc | 4.13 | 0.79 | 4.4 | 3.5 |
| Triammonium citrate-DHA[f] | 4.45 | 0.96 | 4.7 | 4.5 |
| Triammonium citrate-DHA | 4.28 | 0.74 | 5.4 | 4.0 |
| Triammonium citrate-DHA-Glycerol[g] | 3.75 | 0.52 | 8.5 | 4.4 |
| Triammonium citrate-DHA-Glycerol[g] | 3.38 | 0.59 | 8.0 | 4.7 |
| Triammonium citrate-DHA-PETol[h] | 4.96 | 0.61 | 10.7 | 6.5 |
| Triammonium citrate-DHA-PETol[h] | 5.23 | 0.65 | 9.4 | 6.1 |
| Triammonium citrate-DHA-PVOH[i] | 5.11 | 0.74 | 15.7 | 11.6 |
| Triammonium citrate-DHA-PVOH[i] | 5.23 | 0.85 | 14.9 | 12.6 |
| Standard PF Binder[j] | 7.22 | 0.75 | 15.9 | 12.0 |
| Standard PF Binder[j] | 8.05 | 0.75 | 18.8 | 14.2 |

[a] From Example 7
[b] From Example 5
[c] Mean of three glass fiber mats
[d] Dex = Dextrose
[e] Fruc = Fructose
[f] DHA = Dihydroxyacetone
[g] Glycerol substituted for 25% of DHA by weight
[h] PETol = Pentaerythritol substituted for 25% of DHA by weight
[i] PVOH = Polyvinyl alcohol (86-89% hydrolyzed polyvinyl acetate, MW ~22K-26K), substituted for 20% of DHA by weight
[j] Ductliner binder

TABLE 8

Testing Results for Cured Blanket from Example 8: Triammonium citrate-Dextrose (1:6) Binder vs. Standard PF Binder

| TEST | Melanoidin- Fiberglass Cured Blanket "BINDER" | PF Binder - Fiberglass Cured Blanket "STANDARD" | BINDER % of STANDARD |
|---|---|---|---|
| Density | 0.65 | 0.67 | 97% |
| Loss on Ignition (%) | 13.24% | 10.32% | 128% |
| Thickness Recovery (dead, in.) | 1.46 | 1.59 | 92% |
| Thickness Recovery (drop, in.) | 1.55 | 1.64 | 94% |
| Dust (mg) | 8.93 | 8.80 | 102% |
| Tensile Strength (lb/in. width) | | | |
| Machine Direction | 2.77 | 3.81 | 73% |
| Cross Machine Dir. | 1.93 | 2.33 | 83% |
| Avg. | 2.35 | 3.07 | 76% |
| Parting Strength (g/g) | | | |
| Machine Direction | 439.22 | 511.92 | 86% |
| Cross Machine Direction | 315.95 | 468.99 | 67% |
| Avg. | 377.59 | 490.46 | 77% |
| Bond Strength (lb/ft$^2$) | 11.58 | 14.23 | 81% |
| Water Absorption (% by weight) | 1.24% | 1.06% | 116% |
| Hot Surface Performance | Pass | Pass | — |
| Product Emissions (at 96 Hours) | | | |
| Total VOCs (μg/m$^3$) | 0 | 6 | 0% |
| Total HCHO (ppm) | 0 | 56 | 0% |
| Total Aldehydes (ppm) | 6 | 56 | 11% |

TABLE 9

Smoke Development on Ignition for Cured Blanket from Example 8: Triammonium citrate-Dextrose (1:6) Binder vs. Standard PF Binder

| External Heat Flux | Average SEA[a] Melanoidin-Fiberglass Cured Blanket | PF Binder-Fiberglass Cured Blanket |
|---|---|---|
| 35 kW/m$^2$ | 2,396 m$^2$/kg | 4,923 m$^2$/kg |
| 35 kW/m$^2$ | 1,496 m$^2$/kg | 11,488 m$^2$/kg |
| 35 kW/m$^2$ | 3,738 m$^2$/kg | 6,848 m$^2$/kg |
|  | Overall Avg. = 2,543 m$^2$/kg | Overall Avg. = 7,756 m$^2$/kg |
| 50 kW/m$^2$ | 2,079 m$^2$/kg | 7,305 m$^2$/kg |
| 50 kW/m$^2$ | 3,336 m$^2$/kg | 6,476 m$^2$/kg |
| 50 kW/m$^2$ | 1,467 m$^2$/kg | 1,156 m$^2$/kg |
|  | Overall Avg. = 2,294 m$^2$/kg | Overall Avg. = 4,979 m$^2$/kg |

[a]SEA = specific extinction area

TABLE 10

Testing Results for Air Duct Board from Example 9: Triammonium citrate-Dextrose (1:6) Binder vs. Standard PF Binder

| TEST | Melanoidin-Fiberglass Air Duct Board "BINDER" | PF Binder - Fiberglass Air Duct Board "STANDARD" | BINDER % of STANDARD |
|---|---|---|---|
| Density | 4.72 | 4.66 | 101% |
| Loss on Ignition (%) | 18.5% | 16.8% | 110% |
| Flexural Rigidity (lb in$^2$/in width) |  |  |  |
| Machine Direction | 724 | 837 | 86% |
| Cross Machine Dir. | 550 | 544 | 101% |
| Avg. | 637 | 691 | 92% |
| Compressive (psi) Resistance at 10% | 0.67 | 0.73 | 92% |
| Compressive (psi) Resistance at 20% | 1.34 | 1.34 | 100% |
| Conditioned Compressive (psi) Resistance at 10% | 0.719 | 0.661 | 109% |
| Conditioned Compressive (psi) Resistance at 20% | 1.31 | 1.24 | 106% |
| Compressive Modulus (psi) | 6.85 | 7.02 | 97% |
| Conditioned Compressive Modulus (psi) | 6.57 | 6.44 | 102% |
| Product Emissions (at 96 Hours) |  |  |  |
| Total VOCs (μg/m$^3$) | 40 | 39 | 102% |
| Total HCHO (ppm) | 0.007 | 0.043 | 16% |
| Total Aldehydes (ppm) | 0.007 | 0.043 | 16% |

TABLE 11

Testing Results for R30 Residential Blanket from Example 10: Triammonium citrate-Dextrose (1:6) Binder vs. Standard PF Binder

| Test | Binder[a] (% of Std) | Binder[b] (% of Std) | Binder[c] (% of Std) | PF Binder Std |
|---|---|---|---|---|
| Thickness recovery (dead, in.): |  |  |  |  |
| 1 week | 10.05 (97%) | 10.36 (99%) | 9.75 (94%) | 10.38 |
| 6 week | 7.17 (91%) | 7.45 (94%) | 7.28 (92%) | 7.90 |
| Thickness recovery (drop, in.): |  |  |  |  |
| 1 week | 11.06 (101%) | 4.23 (102%) | 11.01 (100%) | 11.00 |
| 6 week | 9.07 (101%) | 9.06 (101%) | 9.31 (103%) | 8.99 |
| Parting Strength (g/g) |  |  |  |  |
| Machine Direction | 214.62 (78%) | 186.80 (68%) | 228.22 (83%) | 275.65 |
| Cross Machine Direction | 219.23 (75%) | 202.80 (70%) | 210.62 (72%) | 290.12 |
| Average | 216.93 (77%) | 194.80 (69%) | 219.42 (77%) | 282.89 |
| Durability of Parting Strength (g/g) |  |  |  |  |
| Machine Direction | 214.62 (84%) | 209.54 (82%) | 259.58 (102%) | 254.11 |
| Cross Machine Direction | 219.23 (87%) | 204.12 (81%) | 221.44 (88%) | 252.14 |
| Average | 216.93 (86%) | 206.83 (82%) | 240.51 (95%) | 253.13 |
| Bond Strength (lb/ft2) | 1.86 (84%) | NM[d] | NM[d] | 2.20 |

TABLE 11-continued

Testing Results for R30 Residential Blanket from Example 10: Triammonium citrate-Dextrose (1:6) Binder vs. Standard PF Binder

| Test | Binder[a] (% of Std) | Binder[b] (% of Std) | Binder[c] (% of Std) | PF Binder Std |
|---|---|---|---|---|
| Dust (mg) | 0.0113 (79%) | 0.0137 (96%) | 0.0101 (71%) | 0.0142 |
| Hot Surface Performance (pass/fail) | Pass | Pass | Pass | Pass |
| Corrosivity (steel) (pass/fail) | Pass | Pass | Pass | NM[d] |

[a]Melanoidin binder; nominal machine condition to produce loss on ignition of 5%
[b]Melanoidin binder; machine adjustment to increase loss on ignition to 6.3%
[c]Melanoidin binder; machine adjustment to increase loss on ignition to 6.6%
[d]Not measured

TABLE 12

Testing Results for R19 Residential Blanket from Example 11 (Batch A-1): Triammonium citrate-Dextrose (1:6) Binder vs. Standard PF Binder

| TEST | Melanoidin- Fiberglass R19 Residential "BINDER" | PF Binder - Fiberglass R19 Residential "STANDARD" | BINDER % of STANDARD |
|---|---|---|---|
| Thickness Recovery (dead, in.): | | | |
| 1 week | 6.02 | 6.05 | 99% |
| 5 week | 6.15 | 6.67 | 92% |
| 6 week | 4.97 | 5.14 | 97% |
| 3 month | 6.63 | 6.20 | 107% |
| Thickness Recovery (drop, in.): | | | |
| 1 week | 6.79 | 6.69 | 101% |
| 4 week | 6.92 | 7.11 | 97% |
| 6 week | 5.83 | 6.07 | 96% |
| 3 month | 7.27 | 6.79 | 107% |
| Dust (mg) | 2.88 | 8.03 | 36% |
| Tensile Strength (lb/in. width) | | | |
| Machine Direction | 2.42 | 3.47 | 70% |
| Cross Machine Dir. | 2.00 | 3.03 | 66% |
| Average | 2.21 | 3.25 | 68% |
| Parting Strength (g/g) | | | |
| Machine Direction | 128.18 | 173.98 | 74% |
| Cross Machine Direction | 118.75 | 159.42 | 74% |
| Average | 123.47 | 166.70 | 74% |
| Durability of Parting Strength (g/g) | | | |
| Machine Direction | 143.69 | 161.73 | 89% |
| Cross Machine Direction | 127.30 | 149.20 | 85% |
| Average | 135.50 | 155.47 | 87% |
| Bond Strength (lb/ft$^2$) | 1.97 | 2.37 | 83% |
| Water Absorption (%) | 7.1 | 7.21 | 98% |
| Hot Surface Performance | Pass | Pass | — |
| Corrosion | Pass | Pass | — |
| Stiffness-Rigidity | 49.31 | 44.94 | 110% |

TABLE 13

Testing Results for R19 Residential Blanket from Example 11: Triammonium citrate-Dextrose (1:6) Binder Variants vs. Standard PF Binder

| Test | Binder Batch A-2[a] (% of Std) | Binder Batch B[a] (% of Std) | Binder Batch C[a] (% of Std) | Binder Batch D[a] (% of Std) | PF Binder Std. |
|---|---|---|---|---|---|
| Thickness recovery (dead, in.): | | | | | |
| 1 week | 5.94 (99%) | 5.86 (98%) | 6.09 (101%) | 6.25 (104%) | 6.01 |
| 6 week | 4.86 (91%) | 5.29 (99%) | 5.0 (93%) | 5.10 (95%) | |

TABLE 13-continued

Testing Results for R19 Residential Blanket from Example 11: Triammonium citrate-Dextrose (1:6) Binder Variants vs. Standard PF Binder

| Test | Binder Batch A-2[a] (% of Std) | Binder Batch B[a] (% of Std) | Binder Batch C[a] (% of Std) | Binder Batch D[a] (% of Std) | PF Binder Std. |
|---|---|---|---|---|---|
| Thickness recovery (drop, in.): | | | | | |
| 1 week | 6.83 (105%) | 6.7025 (103%) | 6.81 (104%) | 6.88 (105%) | 6.00 |
| 6 week | 5.76 (96%) | 6.02 (100%) | 5.89 (98%) | 6.00 (100%) | |
| Tensile Strength (lb/in) | | | | | |
| Machine Direction | 1.28 (36%) | 1.40 (39%) | 1.71 (48%) | 1.55 (43%) | 3.58 |
| Cross Machine Direction | 1.65 (71%) | 1.21 (52%) | 1.12 (48%) | 1.12 (48%) | 2.31 |
| Average | 1.47 (50%) | 1.31 (44%) | 1.42 (48%) | 1.34 (45%) | 2.95 |
| Parting Strength (g/g) | | | | | |
| Machine Direction | 111.82 (42%) | 164.73 (62%) | 136.00 (51%) | 164.56 (62%) | 264.81 |
| Cross Machine Direction | 140.11 (85%) | 127.93 (78%) | 126.46 (77%) | 108.44 (66%) | 164.60 |
| Average | 125.97 (59%) | 146.33 (68%) | 131.23 (61%) | 136.50 (64%) | 214.71 |
| Durability of Parting Strength (g/g) | | | | | |
| Machine Direction | 138.55 (72%) | 745.62 (76%) | 113.37 (59%) | 176.63 (92%) | 191.20 |
| Cross Machine Direction | 158.17 (104%) | 116.44 (77%) | 97.10 (64%) | 162.81 (107%) | 151.49 |
| Average | 148.36 (86%) | 131.03 (76%) | 105.24 (61%) | 169.72 (99%) | 171.35 |
| Bond Strength (lb/ft2) | 1.30 (52%) | 1.50 (60%) | 1.60 (64%) | 1.60 (64%) | 2.50 |
| Dust (mg) | 0.0038 (86%) | 0.0079 (179%) | 0.0053 (120%) | 0.0056 (126%) | 0.0044 |
| Stiffness-Rigidity (degrees) | 57.50 (N/A) | 55.50 (N/A) | 61.44 (N/A) | 59.06 (N/A) | 39.38 |

[a]Melanoidin binder

TABLE 14

GC/MS Analysis of Gaseous Compounds Produced During Pyrolysis of Cured Blanket (from Example 8) Prepared With Ammonium Citrate-Dextrose (1:6) Binder

| Retention Time (min) | Tentative Identification | % Peak Area |
|---|---|---|
| 1.15 | 2-cyclopenten-1-one | 10.67 |
| 1.34 | 2,5-dimethyl-furan | 5.84 |
| 3.54 | furan | 2.15 |
| 3.60 | 3-methyl-2,5-furandione | 3.93 |
| 4.07 | phenol | 0.38 |
| 4.89 | 2,3-dimethyl-2-cyclopenten-1-one | 1.24 |
| 5.11 | 2-methyl phenol | 1.19 |
| 5.42 | 4-methyl phenol | 2.17 |
| 6.46 | 2,4-dimethyl-phenol | 1.13 |
| 10.57 | dimethylphthalate | 0.97 |
| 17.89 | octadecanoic acid | 1.00 |
| 22.75 | erucylamide | 9.72 |

TABLE 15

GC/MS Analysis of Gaseous Compounds Produced During Thermal Curing of Pipe Insulation Uncured (from Example 12) Prepared With Ammonium Citrate-Dextrose (1:6) Binder

| Retention Time (min) | Identification | % Peak Area |
|---|---|---|
| 1.33 | 2,5-dimethylfuran | 1.02 |
| 2.25 | furfural OR 3-furaldehyde | 2.61 |
| 2.48 | 2-furanmethanol OR 3-furanmethanol | 1.08 |
| 3.13 | 1-(2-furanyl)-ethanone | 0.52 |
| 3.55 | furan | 4.92 |
| 3.62 | 2-pyridinecarboxyaldehyde | 0.47 |
| 3.81 | 5-methylfurfural | 3.01 |
| 3.99 | furancarboxylic acid, methyl ester | 0.34 |
| 4.88 | 3,4-dimethyl-2,5-furandione | 0.53 |
| 5.41 | 2-furancarboxylic acid | 1.01 |
| 6.37 | 2-amino-6-hydroxymethylpyridine | 1.08 |
| 6.67 | 6-methyl-3-pyridinol | 0.49 |
| 7.59 | 2-furancarboxaldehyde | 0.47 |
| 7.98 | picolinamide | 0.24 |
| 10.34 | 2H-1-benzopyran-2-one | 0.23 |
| 16.03 | hexadecanoic acid | 0.21 |
| 17.90 | octadecanoic acid | 2.97 |
| 22.74 | erucylamide | 10.02 |

While certain embodiments of the present invention have been described and/or exemplified above, it is contemplated that considerable variation and modification thereof are possible. Accordingly, the present invention is not limited to the particular embodiments described and/or exemplified herein.

What is claimed is:

1. A composition, comprising:
  a nitrogenous polymer binder disposed on a collection of cellulosic fibers, wherein
  (i) the nitrogenous polymer binder includes melanoidins generated from the reaction of a carbohydrate reactant and an amine reactant,
  (ii) a portion of the melanoidins of the nitrogenous polymer binder are cross-linked through a monomeric polycarboxylic acid reactant, and
  (iii) the ratio of the number of moles of the monomeric polycarboxylic acid reactant to the number of moles of carbohydrate reactant is from about 1:4 to about 1:15.

2. The composition of claim 1, wherein the carbohydrate reactant is a monosaccharide in its aldose or ketose form.

3. The composition of claim 1, wherein the amine reactant is ammonia.

4. The composition of claim 1, wherein the monomeric polycarboxylic acid is selected from a dicarboxylic acid, a tricarboxylic acid, a tetracarboxylic acid, and a pentacarboxylic acid or anhydrides or combinations thereof.

5. The composition of claim 1, wherein the carbohydrate reactant is selected from the group consisting of dextrose, xylose, fructose, dihydoxyacetone, and mixtures thereof.

6. The composition of claim 1, wherein the polycarboxylic acid reactant is selected from the group consisting of citric acid, maleic acid, tartaric acid, malic acid, succinic acid, and mixtures thereof.

7. The composition of claim 1, wherein the polycarboxylic acid reactant is citric acid.

8. The composition of claim 1, wherein the carbohydrate reactant is dextrose.

9. The composition of claim 1, wherein the nitrogenous polymer binder is of the type formed in a dehydrated state.

* * * * *